United States Patent [19]
Reichler et al.

[11] Patent Number: 5,578,270
[45] Date of Patent: Nov. 26, 1996

[54] SYSTEM FOR NUCLEIC ACID BASED DIAGNOSTIC ASSAY

[75] Inventors: Allen S. Reichler, Owing Mills; David J. Antol, Baldwin; Michael L. Lamos, Westminster, all of Md.; Peter A. Bourdelle, Glen Rock; Scott D. Hildebrand, Red Lion, both of Pa.

[73] Assignee: Becton Dickinson and Company, Franklin Lakes, N.J.

[21] Appl. No.: 409,821

[22] Filed: Mar. 24, 1995

[51] Int. Cl.⁶ .................................................. G01N 21/05
[52] U.S. Cl. .......................... 422/67; 422/81; 422/103; 436/49; 436/54
[58] Field of Search .................. 436/49, 54; 422/67, 422/68.1, 81, 100, 103

[56] References Cited

U.S. PATENT DOCUMENTS

| | | | |
|---|---|---|---|
| 4,598,049 | 7/1986 | Zelinka et al. | 422/62 |
| 4,785,677 | 11/1988 | Higo | 422/100 |
| 5,361,805 | 11/1994 | Mayeux | 137/885 |

*Primary Examiner*—Lyle A. Alexander
*Attorney, Agent, or Firm*—Alan W. Fiedler

[57] ABSTRACT

An automated system is provided for carrying out nucleic acid based assays on a plurality of liquid samples with little or no intervention by a human operator. The system includes at least one reaction station adapted to hold and apply controlled amounts of heat to a plurality of reaction devices in which the liquid samples are receivable. Each of the reaction devices includes a sample area for receiving a liquid sample, a reaction area into which the liquid sample is movable to carry out a nucleic acid decontamination or amplification reaction on the sample, and a pneumatic port for allowing air to be aspirated from and dispensed into the reaction device to move the sample between the sample area and the reaction area. A robotically controlled aspiration and dispensing head is adapted to move into contact with the pneumatic ports of the reaction devices, and to aspirate air from and dispense air into the pneumatic ports of the reaction devices in order to move the liquid samples between the sample and reaction areas of the reaction devices. A programmable control system is provided for causing the robotically controlled aspiration and dispensing head to move into contact with the pneumatic ports of the reaction devices, and to aspirate air from and dispense air into the reaction devices in order to cause the desired movement of the liquid samples within the reaction devices. The robotically controlled aspiration and dispensing head is also adapted to transfer the liquid samples to and from the reaction devices using disposable pipettes, and to introduce liquid reagents into the reacted samples after the samples have been transferred from the reaction devices to separate assay devices. A robotically controlled wash head is also provided to aspirate and dispense wash fluids and reagent fluids from the assay devices.

21 Claims, 29 Drawing Sheets

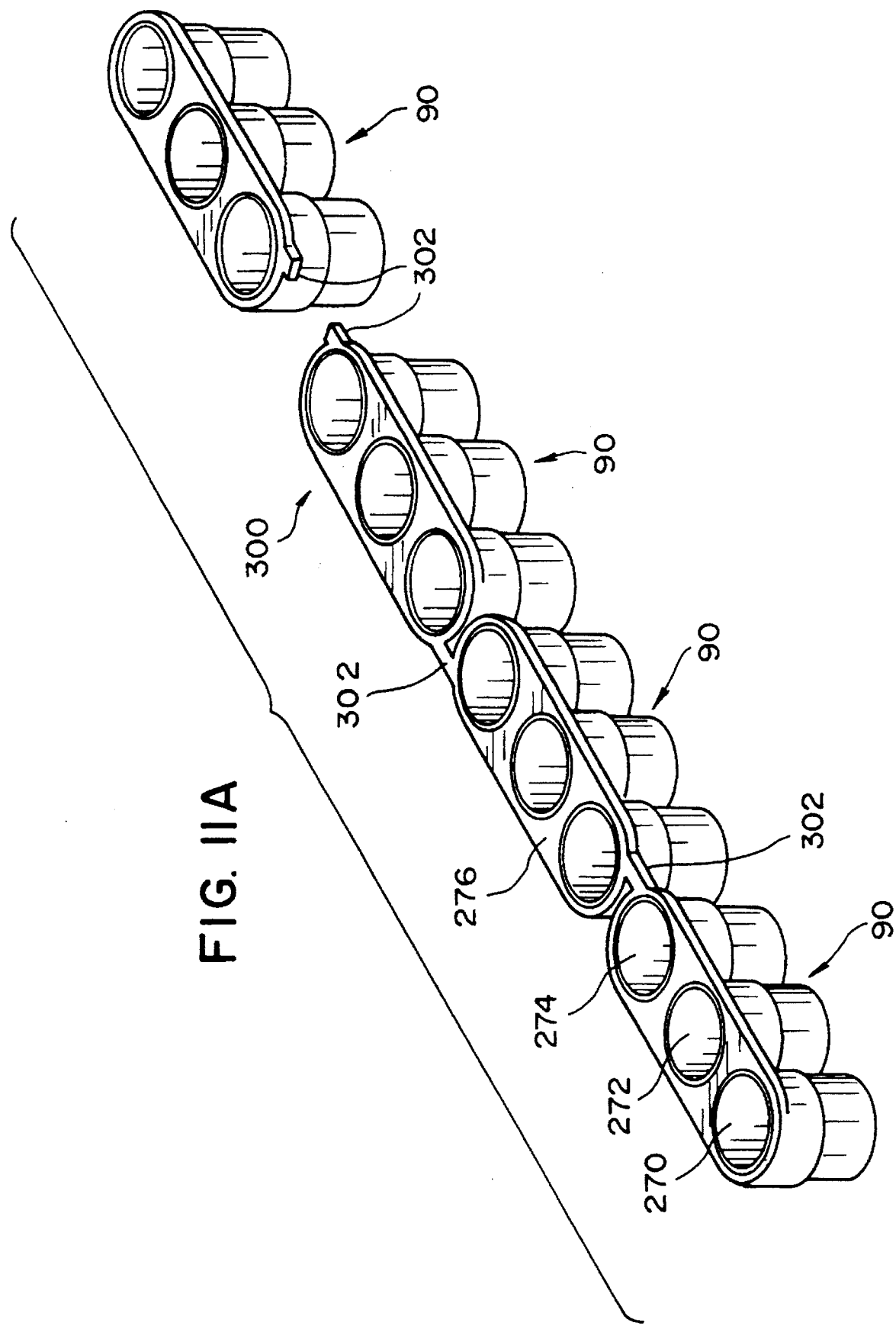
FIG. IIA

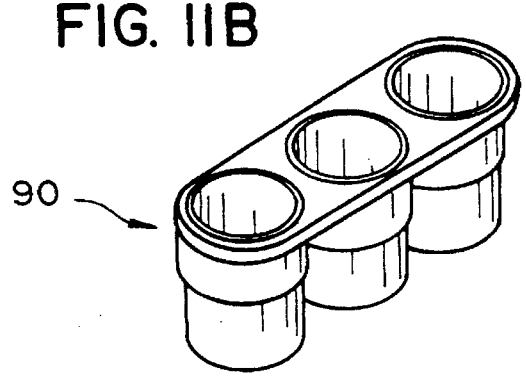
FIG. IIB
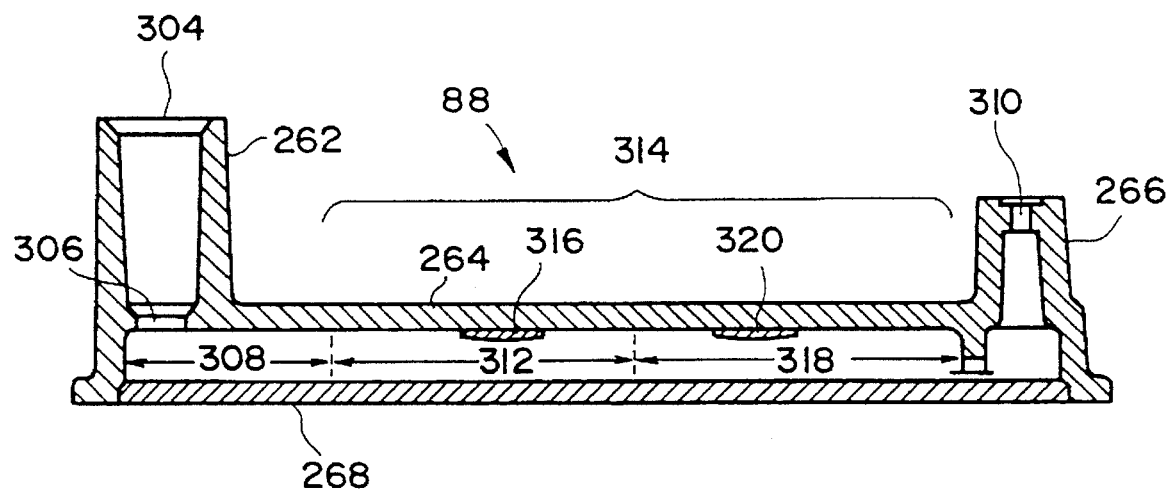
FIG. 12

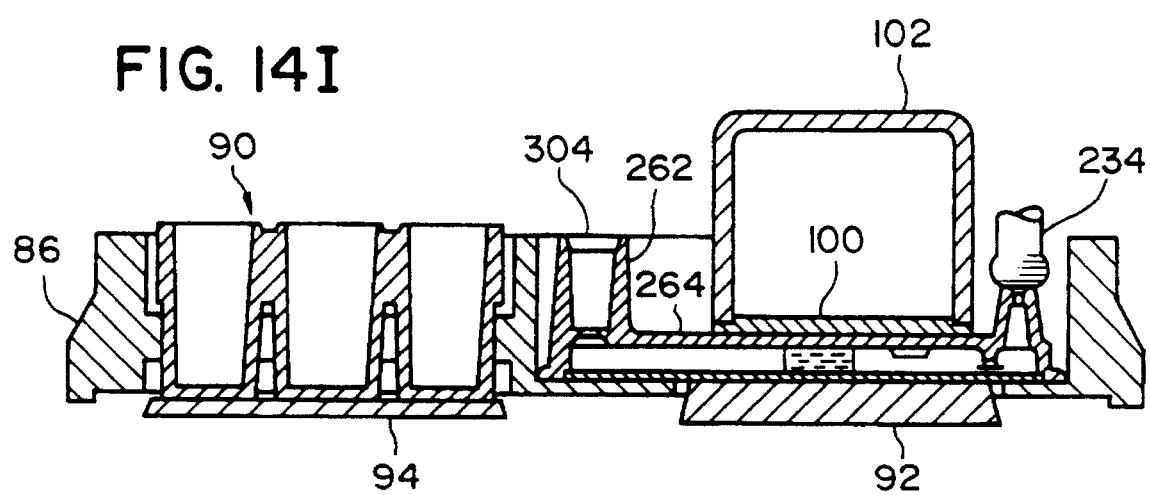
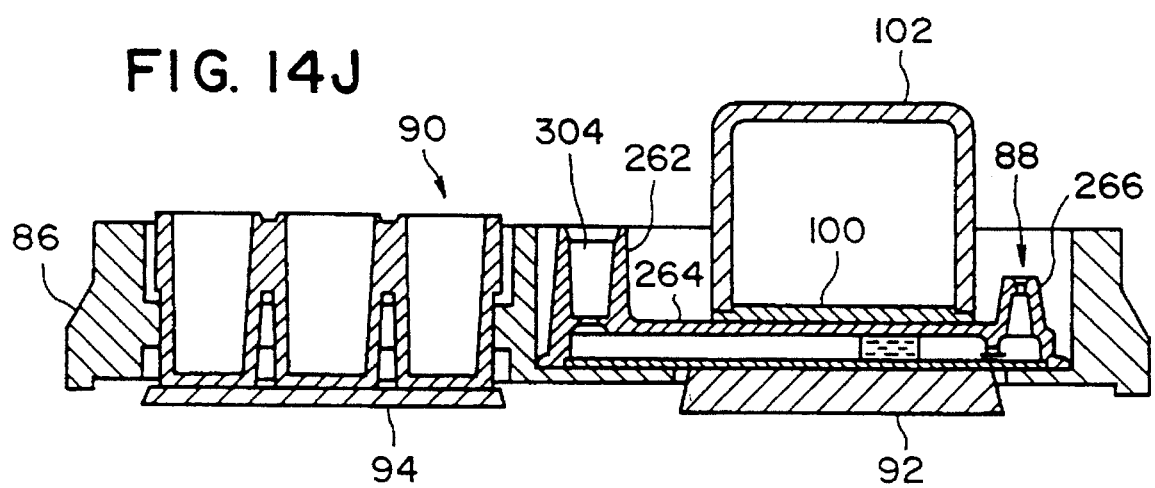
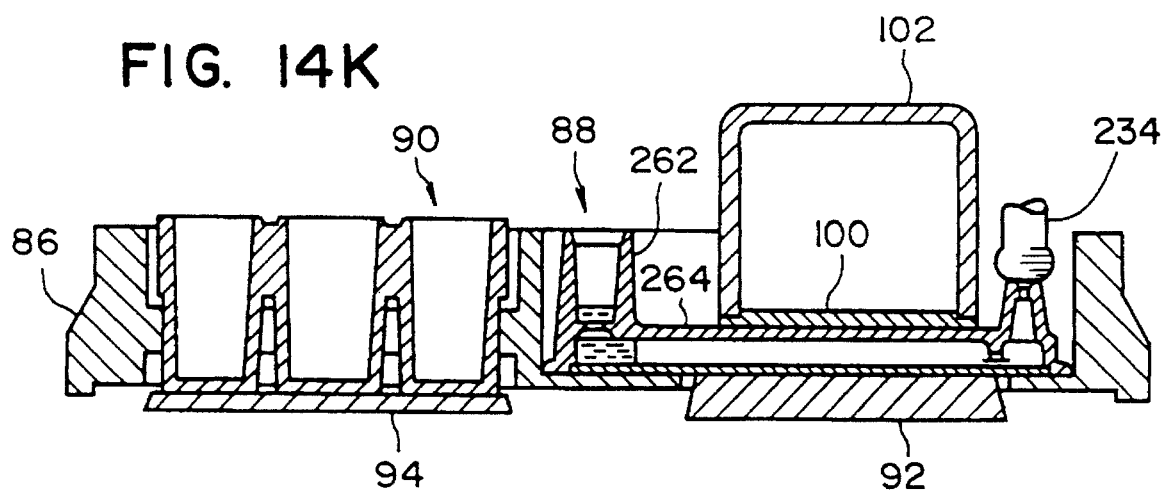

SYSTEM FOR NUCLEIC ACID BASED DIAGNOSTIC ASSAY

CROSS-REFERENCE TO RELATED APPLICATIONS

Related subject matter is disclosed in a copending patent application of Allen S. Reichler et al, filed on even date herewith and entitled "Nucleic Acid Amplification Method and Apparatus" (Attorney's File 2573-P1), and in a copending U.S. patent application of Michael L. Lamos et al, filed on even date herewith and entitled "Pipette Tip" (Attorney's File P-3193), both of said applications being expressly incorporated herein by reference.

FIELD OF THE INVENTION

The present invention relates to an automated system for carrying out reactions on a plurality of liquid samples, and particularly relates to an automated system in which robotically controlled fluid aspirating and dispensing heads executing programmed movements are used to carry out nucleic acid based diagnostic assays on a plurality of liquid biological samples with little or no intervention by a human operator.

BACKGROUND OF THE INVENTION

In the clinical diagnosis of respiratory bacterial diseases, such as tuberculosis, a sample of sputum or other body fluid obtained from the patient is cultured in an agar growth medium to test for the presence of the particular bacterium of interest. Unfortunately, this is a relatively time-consuming process, generally requiring several days to produce a definitive result. During this time, a patient suspected of having tuberculosis, for example, must be isolated to prevent further spread of the disease.

The advent of DNA probes, which can identify a specific bacterium by testing for the presence of a unique DNA sequence in the sample obtained from the patient, has greatly increased the speed and reliability of clinical diagnostic testing. A test for the tuberculosis mycobacterium, for example, can be completed within a matter of hours using DNA probe technology. This allows treatment to begin more quickly and avoids the need for long patient isolation times.

In the use of DNA probes for clinical diagnostic purposes, a nucleic acid amplification reaction is carried out in order to multiply the target nucleic acid into millions of copies or amplicons. Examples of nucleic acid amplification reactions which can be used include strand displacement amplification (SDA) and polymerase chain reaction (PCR). Unfortunately, nucleic acid amplification reactions can become contaminated with the amplicons produced by previous amplification reactions. The contaminating amplicons can, in turn, contaminate new samples entering the lab, leading to false positive diagnoses.

Decontamination techniques have been developed in which contaminating amplicons produced by previous amplification reactions are recognized and destroyed. By carrying out a decontamination reaction prior to amplification, the possibility that a contaminating amplicon will be recognized as a target nucleic acid is greatly decreased. However, because decontamination and amplification reagents are often not compatible with each other and require their own reaction conditions, they must often be carried out in separate containers. In transferring the sample from one container to another, recontamination can occur.

In order to minimize contamination problems, separate areas of a clinical diagnostic laboratory are often reserved for sample preparation, amplification/decontamination and assay (detection). Although this is an effective safeguard, it is very labor-intensive and offsets some of the advantages offered by DNA probe techniques. Automation of all or part of the procedure would be desirable, but this is difficult to achieve when many processing steps are involved and the potential for cross-contamination between samples is great.

In the aforementioned copending patent application of Allen S. Reichler et al entitled "Nucleic Acid Amplification Method and Apparatus", a disposable, single-use apparatus or module is described which allows decontamination and amplification of a liquid biological sample to be carried out within the confines of a single container. In general, the disclosed apparatus includes a sample area for receiving a liquid biological sample, at least one reaction area in fluid communication with the sample area, a pneumatic area in pneumatic communication with the reaction area and the sample area, and a pneumatic port in the pneumatic area for allowing connection of the apparatus or module to a pneumatic aspiration/dispensing means. Operation of the pneumatic aspiration/dispensing means causes the liquid biological sample to flow between the sample area and the reaction area, and between different zones in the reaction area, in a controlled manner. Reagents necessary for the decontamination and amplification reactions are affixed to separate, discrete locations within the reaction area, and are contacted by the liquid biological sample at different times under the control of the pneumatic aspiration/dispensing means.

It is an object of the present invention to provide an automated system for carrying out reactions on a plurality of liquid samples using disposable, single-use modules of the general type described above.

It is another object of the invention to provide an automated system for carrying out reactions on a plurality of liquid samples, particularly nucleic acid based diagnostic assays, with little or no intervention by a human operator.

It is further object of the invention to provide an automated system for carrying out reactions on a plurality of liquid samples, particularly nucleic acid based diagnostic assays, while minimizing the potential for cross-contamination between different samples.

It is a still further object of the invention to provide improved methods for carrying out reactions on a plurality of liquid samples, particularly nucleic acid based diagnostic assays, which methods can be carried out using the exemplary apparatus disclosed and claimed herein.

SUMMARY OF THE INVENTION

In accordance with one aspect of the present invention, an automated system for carrying out reactions on a plurality of liquid samples comprises a reaction station adapted to hold a plurality of reactions devices in which the liquid samples are receivable. Each of the reaction devices includes a sample area for receiving a liquid sample, a reaction area into which the liquid sample is movable to carry out a reaction on the sample, and a pneumatic port for allowing air to be aspirated from and dispensed into the reaction device to move the liquid sample between the sample area and the reaction area. A robotically controlled aspiration and dispensing head is adapted to move into contact with the pneumatic ports of the reaction devices, and to aspirate air from and dispense air into the pneumatic ports of the reaction devices in order to move the liquid sample in the reaction devices between the sample and reaction areas of the reaction devices. A programmable control device is provided for causing the robotically controlled aspiration and dispensing head to move into contact with the pneumatic ports of the reaction devices, and to aspirate air from and dispense air into the reaction devices in order the move the liquid samples between the sample areas and the reaction areas of the reaction devices.

In another aspect of the present invention, a reaction station for use in an automated system for carrying out reaction on a plurality of liquid samples comprises a fixed heating platen for heating the liquid samples, and a removable tray positionable on the heating platen. The removable tray is adapted to hold a plurality of reaction devices in which the liquid samples are receivable. A locating device is provided for locating the removable tray at a predetermined position on the heating platen.

In a further aspect of the present invention, an assembly for use in an automated system for carrying out reactions on a plurality of liquid samples comprises a plurality of reaction devices in which the liquid samples are receivable, and a tray adapted to hold the plurality of reaction devices. The reaction devices have substantially flat bottom surfaces through which heat can be applied to the liquid samples. The tray is formed with shaped slots or cavities for receiving each of the reaction devices in a predetermined position and orientation, and with cut-out portions for allowing the substantially flat bottom surfaces of the reaction devices to make direct contact with a heating platen.

In a still further aspect of the present invention, an assay device for use in an automated system for carrying out reactions on a liquid sample comprises a plurality of connected wells for receiving portions of the liquid sample. Each of the wells has an open top for admitting a portion of the liquid sample, a substantially flat bottom surface for making contact with a heating platen, and interior walls coated with a diagnostic reagent.

The present invention is also directed to methods for carrying out reactions on liquid samples, which methods may be implemented using the exemplary apparatus disclosed and claimed herein.

BRIEF DESCRIPTION OF THE DRAWINGS

The various objects, advantages and novel features of the invention will be more readily apprehended from the following detailed description when read in conjunction with the appended drawings, in which:

FIGS. 11A and 11B are a perspective views illustrating two possible embodiments of the assay devices;

FIG. 12 is an enlarged cross-sectional view of one of the reaction devices, illustrating the placement of the decontamination and amplification reagents in the reaction area;

Throughout the drawings, like reference numerals will be understood to refer to like parts and components.

DETAILED DESCRIPTION OF THE PREFERRED EMBODIMENTS

Figure 1:
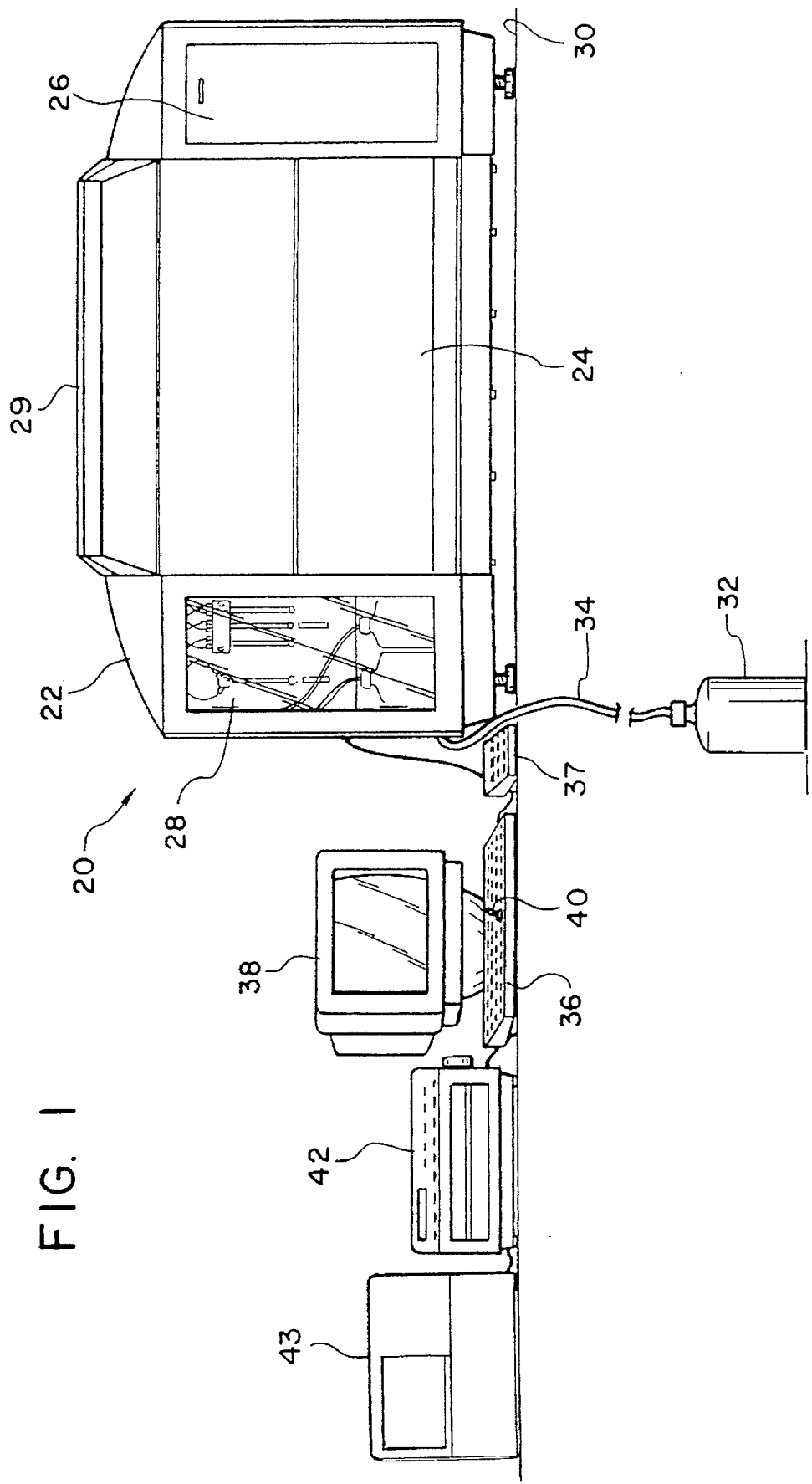
FIG. 1 is a perspective view of the principal components of an automated system for carrying out nucleic acid based diagnostic assays in accordance with a preferred embodiment of the present invention.

FIG. 1 illustrates an automated nucleic acid based diagnostic assay system 20 constructed in accordance with a preferred embodiment of the present invention. The system includes a cabinet or enclosure 22 which houses the principal components of the system and the liquid samples to be assayed. At the front of the cabinet 22 is a bottom-hinged door 24 which affords access to the cabinet interior, a slide-out drawer 26 which provides access to the system computer, and a side-hinged clear plastic door 28 which allows access to the containers and syringes used for dispensing fluids. A rear-hinged top door 29 is also provided to improve the operator's access to the interior of the cabinet 22. The doors 24, 28 and 29 and the drawer 26 are shown in their closed positions in FIG. 1. The cabinet 22 has dimensions suitable for placement on a laboratory counter or tabletop 30, as shown, for convenient access by laboratory personnel. Waste fluids that are produced by the system 20 are pumped into a waste bottle 32 by means of a flexible waste tube 34 that is coupled to a fitting (not shown) on the left side of the cabinet 22. The system computer (not shown) housed within the slide-out drawer 26 is connected to a keyboard 36 (with an integral mouse or trackball 40), a numeric keypad 37, a video display unit 38, and a printer 42. These components are provided to allow laboratory personnel to program and initialize the system 20, to select among various system options, and to monitor the status of the system during automated operation. Also connected to the system computer is a luminometer 43 that performs a chemiluminescent detection step at the conclusion of the automated assay.

Figure 2:
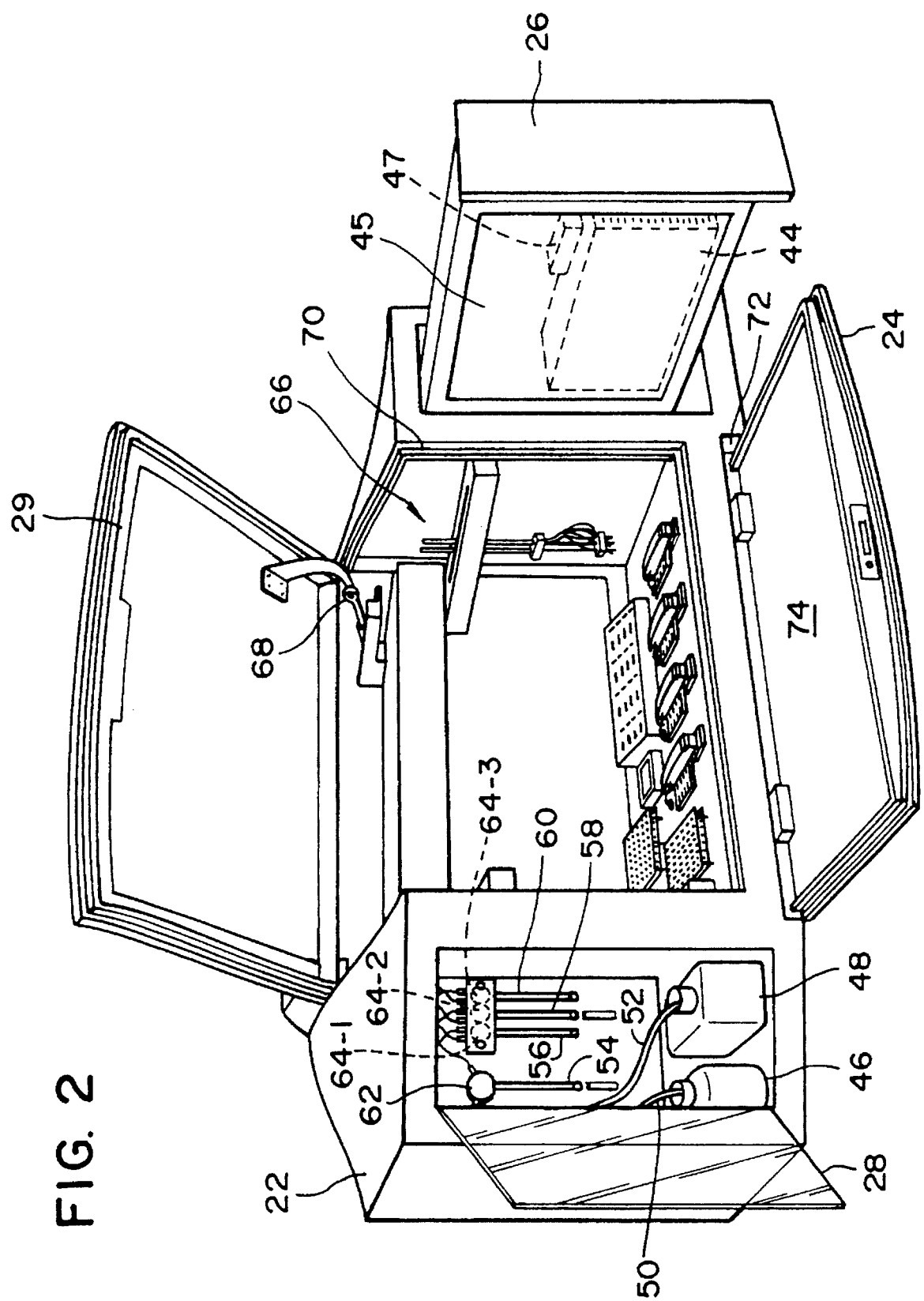
FIG. 2 is a perspective view of the cabinet or enclosure in which the assays are performed, with the doors of the apparatus shown in an open position to illustrate certain internal details.

FIG. 2 is a detailed perspective view of the cabinet 22, with the slide-out drawer 26 and doors 24, 28 and 29 shown in the open position. Housed within the slide-out drawer 26 behind a removable panel 45 is the system computer 44, which is preferably a Model MS-32 computer manufactured by Advance Modular Solutions of Acton, Mass. The system computer 44 includes a floppy disk drive 47 which may be used for installing software updates. At the left-hand side of the cabinet 22, the area behind the transparent door 28 houses a first fluid supply bottle 46 for containing a system fluid (typically consisting of water with preservatives) and a second fluid supply bottle 48 for containing a stringency wash solution. The tubes 50 and 52 allow fluids to be drawn from the bottles 46 and 48, respectively, by means of automatically controlled syringe pumps or diluters 54 and 56-60. Fluid valves 62 and 64-1 through 64-3 (the latter shown behind a cover plate 64), also controlled automatically by the system 20, allow the syringes 54 and 56-60 to withdraw fluids from the supply bottles 46 and 48, and to dispense these fluids at predetermined locations within the processing area 66 of the cabinet 22 during the automated assay procedure.

With continued reference to FIG. 2, the upper door 29 is held in its open or elevated position by means of a holding device 68 that is carried by the frame of the cabinet 22. The front door 24, which interfits with the upper door 29 and cabinet opening 70 in a light-tight clamshell manner, is held securely in its horizontal open position by means of stops (not shown) and is slidable by a short distance into a slot 72 located at the bottom forward edge of the cabinet 22. In this orientation, the flat interior surface 74 of the door 24 provides a convenient work surface for laboratory personnel during installation and removal of components from the processing area of the cabinet 22. The light-tight fit between the doors 24 and 29 and the cabinet opening 70, which is made possible by complementary labyrinthine seals formed around their peripheries, allows for the possibility of carrying out chemiluminescent detection within the cabinet 22 rather than in a separate luminometer 43.

Figure 3:
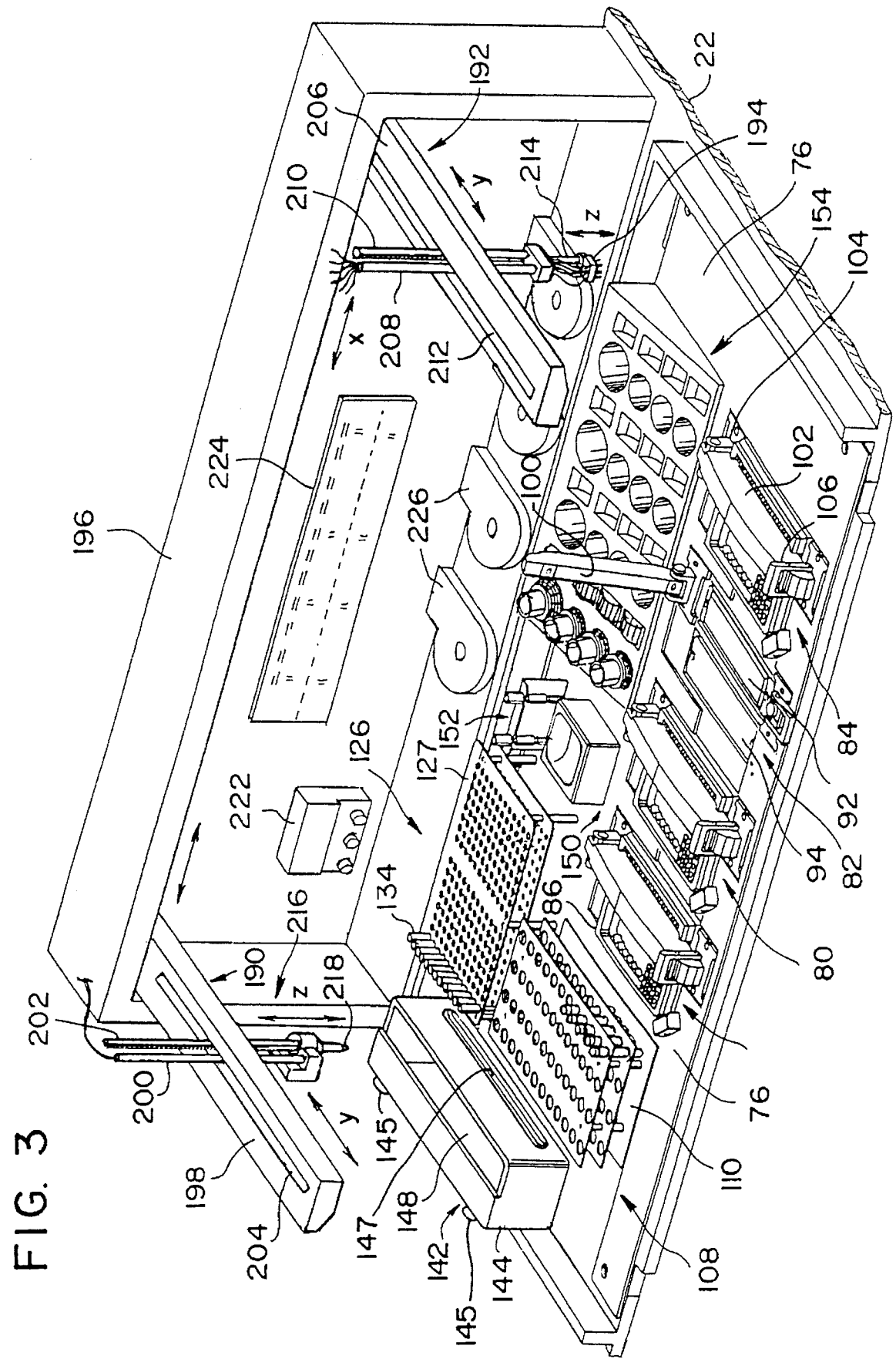
FIG. 3 is a detailed perspective view of the cabinet interior, illustrating the stations provided in the system and the robotic arms which perform various programmed functions at these stations.
Figure 4:
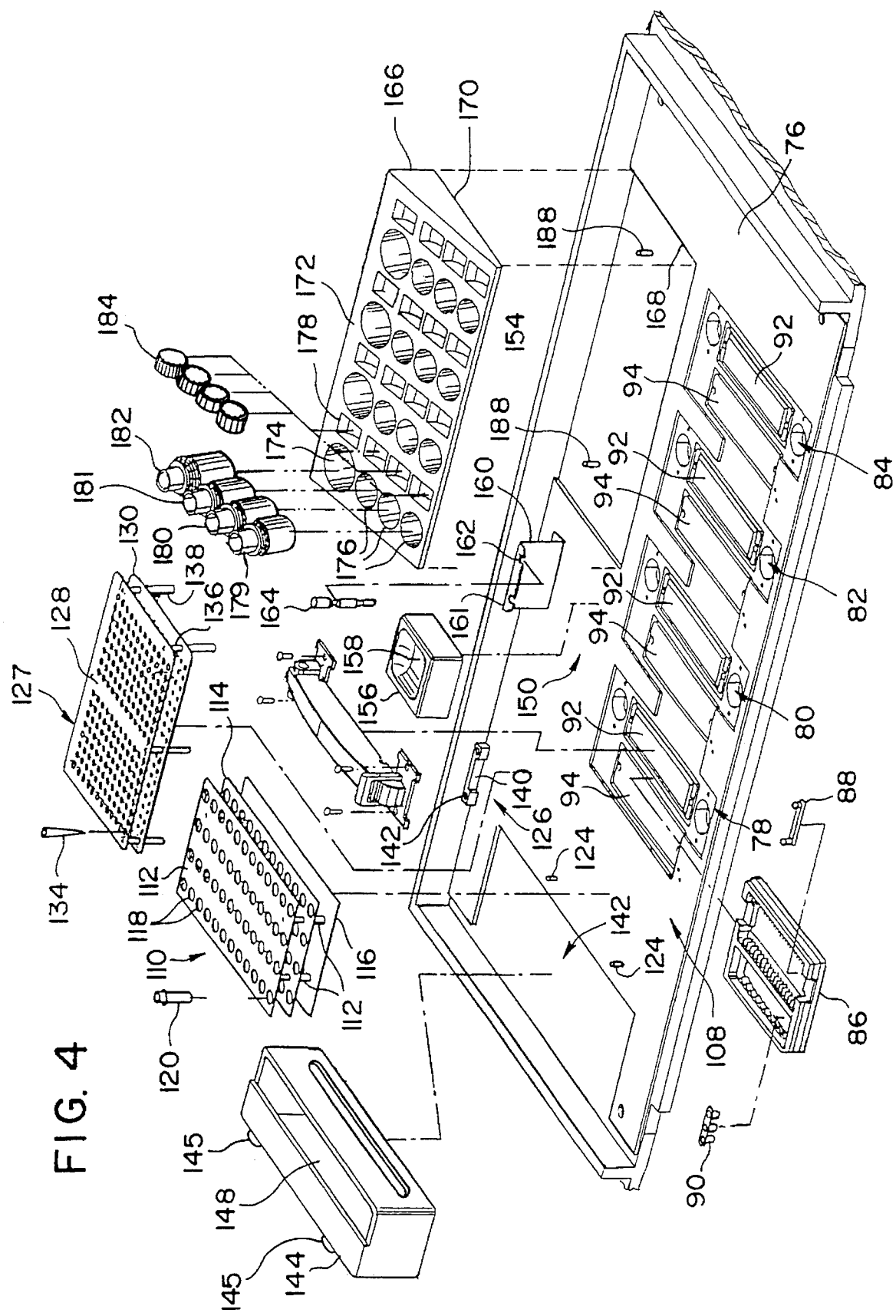
FIG. 4 is an exploded perspective view similar to that of FIG. 3, illustrating the manner in which the components of certain stations are removable.

The components located in the processing area 66 of the cabinet 22 are shown in FIGS. 3 and 4. In general, the processing area 66 is defined by a flat locator plate 76 which is mounted on the deck or base plate 77 of the cabinet 22. Various stations are provided on the locator plate 76, or on the deck 77 within cut-out areas of the locator plate 76, for the components required for carrying out the desired nucleic acid based assay. Included among the stations are four identical reaction stations 78, 80, 82 and 84, where the principal processing steps are carried out on the liquid biological samples to be assayed. Each reaction station receives a removable tray 86 which holds a plurality of reaction devices 88 and a corresponding plurality of assay devices 90. In the preferred embodiment, twelve reaction devices 88 and twelve assay devices 90 are carried by each tray 86. The reaction devices 88 and assay devices 90 are heated from the bottom by elongated heating platens 92 and 94, respectively, which are installed in the deck or base plate 77. The trays 86 are formed with cut-out portions 96 and 98 for allowing direct contact between the bottoms of the devices 88 and 90 and their corresponding heating platens 92 and 94. In addition, the top surfaces of the reaction devices 88 are heated by an upper heating platen 100 which is carried by a pivotable arm 102. The arms 102 are carried by a hinges 104 located at the rear of the reaction stations 78-84, and are locked in the downward position by means of pivotable U-shaped clamps 106 located at the forward end of the reaction stations 78-84. The pivotable arms 102 serve the dual purpose of bringing the upper heating platens 100 firmly into contact with the upper surfaces of the reaction devices 88, and locking the trays 86 into position on the deck or base plate 76. For illustrative purposes, the third reaction station 82 in FIG. 3 is shown with the pivotable arm 102 in the open position and the tray 86 removed, and both the arms 102 and trays 86 have been deleted for all but the first reaction station 78 in FIG. 4.

Immediately to the left of the first reaction station 78 in FIGS. 3 and 4, a sample tube station 108 is provided. The sample tube station includes a removable metal rack 110 comprising three spaced-apart metal plates 112, 114 and 116. The two upper plates 112 and 114 are formed with rows of aligned apertures 118 which receive and locate a plurality of sample tubes 120. The bottom plate 116 does not include apertures and serves as a base for supporting the sample tubes 120. The metal plates 112, 114 and 116 are held in a parallel, spaced-apart relationship by means of metal spacers 122. The sample tube rack 110 is removable as a whole from the reaction area 66 of the cabinet 22, as indicated in the exploded view of FIG. 4. The locator plate 76 includes a pair of upstanding metal pins 124 which engage corresponding apertures (not shown) in the bottom plate 116 of the sample rack 110 in order to locate the rack 110 in a predetermined position on the deck 76. In practice, the rack 110 will ordinarily be removed from the cabinet 22 for filling before the start of a nucleic acid assay, and then placed in the position defined by the pins 124 after sample tubes 120 containing the liquid biological samples to be assayed have been placed into the apertures 118. Only a few sample tubes 120 have been shown in FIGS. 3 and 4 for clarity, although it will be understood that the rack 10 can accommodate as many sample tubes 120 as there are apertures 118 in each of the plates 112 and 114. The number of sample tubes 120 used during any given assay will, of course, depend upon the number of liquid biological samples to be assayed.

Located rearwardly of the sample tube station 108 in FIGS. 3 and 4 is a disposable pipette tip station 126. The disposable pipette tip station 126 includes a rack 127 consisting of a pair of parallel, spaced-apart metal plates 128 and 130 which are formed with aligned rows of apertures 132 for receiving and locating a plurality of disposable pipette tips 134. The plates 128 and 130 are held apart by metal spacers 136, and the rack 127 as a whole is supported on the locator plate 76 by means of six metal supports 138. A metal locating fixture 140 is affixed to the locator 76 and contains holes 142 for receiving two of the six metal supports 138 of the rack 127 (specifically, the left-hand and middle supports adjoining the rear of the locator plate 76). In this way, the rack 127 is located at a known position on the locator plate 76, and the same is true of the individual disposable pipette tips 134. As indicated in FIG. 4, the disposable pipette tip rack 127 is removable from the deck 76 to make it easier to replenish the supply of disposable pipette tips 134. Although only a few disposable pipette tips 134 are illustrated in FIGS. 3 and 4 for clarity, it will be understood that a large number of disposable pipette tips (typically 192 or approximately 4 per sample in the illustrated embodiment) will ordinarily be provided in the rack 127.

As will be described in some detail hereinafter, the disposable pipette tips 134 are used by the system 20 to aspirate and dispense both the liquid biological samples themselves and various reagents that are used during the nucleic acid assay. For this purpose, the disposable pipette tips 134 may be of the conventional type, consisting of autoclavable polypropylene with a maximum volume of 300 microliters (μL). However, in order to prevent sample and reagent fluids from being drawn into the robotic aspiration and dispensing system (to be described shortly) with which the disposable pipette tips 134 are used, each tip 134 is modified by providing a plug or insert of filter material (not shown) near its upper end. The filter material allows air to pass for pneumatic aspiration and dispensing purposes, but blocks the passage of sample and reagent fluids. The filter material is described in detail in the aforementioned copending patent application of Michael L. Lamos et al, entitled "Pipette Tip" (Attorney's File P-3193), which is incorporated herein by reference.

Disposable pipette tips are conventionally sold in plastic boxes with cavities or apertures for holding the tips in a rectangular array. If desired, a conventional plastic box of this type may be used in place of the metal rack 127 shown in FIGS. 3 and 4. An example of a disposable pipette tip box of the type contemplated is disclosed in U.S. Pat. No. 4,577,760, to Rainin et al, which is incorporated herein by reference.

To the left of the sample tube station 108 and disposable pipette tip station 126 in FIGS. 3 and 4 is a pipette tip disposal station 142. The pipette tip disposal station 142 comprises a rectangular box 144 which is supported on the deck or base plate 77 in a shallow cut-out area 146 of the locator plate 76. The rectangular box 144 is closed on all sides, except for a slot or opening 148 which occupies the top right-hand area of the box and extends from front to rear. The slot or opening 148 allows used pipette tips 134 to be dropped or ejected into the box 144 by a robotic aspiration and dispensing arm, as will be described shortly. In the preferred embodiment, the box 144 has an internal volume sufficient to contain approximately 384 disposable pipette tips. When the box 144 has reached its maximum capacity, it can be removed and emptied by laboratory personnel as shown in FIG. 4. For convenience in grasping the box 144 during removal, foam spacers 145 are provided o the left side of the box 144 to separate the box 144 from the adjacent interior wall (not shown) of the cabinet 22, and an elongated groove 147 serving as a finger grip is formed along the lower right-hand side of the box 144.

With continued reference to FIGS. 3 and 4, the reaction area 66 of the cabinet 22 also includes a purging station 150, a docking station 152 for pneumatic aspiration and dispensing pipettes, and a reagent station 154. The purging station 150 includes a free-standing wash cup 156, which is generally rectangular in shape with a cavity or depression 158 in its upper surface to provide a fluid receptacle. The wash cup 156 collects fluids which are discharged during periodic purging of the robotic arms used in the reaction area 66 of the cabinet 22, and may be removed from the deck 76 for cleaning as shown in FIG. 4. The docking station 152 includes a metal bracket 160 which is affixed to the deck 76 at a location behind the purging station 150. The bracket 160 has a forwardly-extending horizontal lip or flange 161 which is formed with a pair of U-shaped notches or cut-outs 162 for releasably carrying a pair of pneumatic aspiration and dispensing pipettes 164. The pneumatic aspiration and dispensing pipettes 164 are used to induce sample fluid movement within the reaction devices 88 at the reaction stations 78–84, as will be described below. The reagent station 154 includes a machined plastic holder 166 which is received in a shallow cut-out area 168 of the locator plate 76. The holder 166 is generally wedge-shaped, with a flat bottom surface 170 and an inclined upper surface 172 in which rows of cavities 174, 176 and 178 are formed for holding open reagent bottles 179, 180, 181 and 182 and the caps 184 which have been removed from these bottles. The reagent bottle cavities 174 and 176 are all cylindrical in shape, with the uppermost cavity 174 in each row being larger in diameter than the remaining cavities 176 in order to hold a larger reagent bottle 182. The cavities 178 for holding the reagent bottle caps 184 are all of the same size, and are semicylindrical in configuration so that the caps 184 are held on their sides as shown. In the specific type of nucleic acid assay to be described below, only four liquid reagents (and hence four reagent bottles) are required. However, the reagent bottle holder 166 is preferably formed with a number of spare reagent bottle and cap cavities, as shown, so that the system 20 can be used for other types of assays in which larger numbers of reagents are required. Alternatively, the spare reagent bottle positions allow the system 20 to be used for carrying out different types of assays on different samples (or groups of samples) at the same time. The reagent bottle holder 166 is removable from the reaction area 66 of the cabinet 22, as illustrated in FIG. 4, for storage, replenishment and cleaning. Apertures (not shown) formed on the bottom surface 170 of the holder 166 are engaged by locating pins 188 affixed to the deck 77 in the cut-out area 168 of the locator plate 76. In this way, both the holder 166 and the individual reagent bottles 179–182 are held at predetermined positions within the reaction area 66. If desired, the machined plastic reagent bottle holder 166 may be replaced with a sheet metal rack having rectangular cut-outs, and the reagent bottles 179–182 may be packaged as a single unit that is received in one of the rectangular cutouts.

In order to transfer the liquid samples and reagents between different containers and locations during the nucleic acid assay, the system 20 includes a pair of programmable, independently movable robotic arms 190 and 192 which are movable in three dimensions above the various stations 78–84, 108, 126, 142, 150, 152 and 154 in FIG. 3. The left-hand arm 190 is referred to as the hydropneumatic aspiration and dispensing arm, and the right-hand arm 192 is referred to as the wash arm. Except for the pneumatic aspiration and dispensing head 216 affixed to the lower end of the arm 190 and the wash head 194 affixed to the lower end of the arm 192, the robotic arms 190 and 192 are conventional. A suitable robotic system including the two robotic arms 190 and 192, a fluid aspiration and dispensing system for the arms, and a programmable control system for controlling the arm movements and fluid aspiration and dispensing functions, is the TECAN Model RSP 9652 automated pipciting instrument manufactured by TECAN AG of Hombrechtikon, Switzerland. Both of the arms 190 and 192 are supported from the rear by means of a horizontal track 196, which allows each arm to be moved independently in the x direction (i.e., in the direction parallel to the rear edge of the locator plate 76) by stepper motors under microprocessor control. Each arm 190 and 192 is cantilevered outwardly from the track 196 toward the forward edge of the locator plate 76. The hydropneumatic aspiration and dispensing arm 190 includes an elongated metal enclosure 198, open at the bottom, which houses a y-z stepper motor drive system for a vertical guide rod 200 and hollow gear rack 202. A slot 204 in the enclosure 198 provides clearance for the movement of the guide rod 200 and gear rack 202 in the y direction (i.e., toward or away from the front edge of the locator plate 76). The guide rod 200 and gear rack 202 are also movable vertically through the slot 204 (i.e., toward or away from the surface of the deck 76) to provide the z-direction movement of the arm 190. The wash arm 192 is generally similar in construction, and includes an elongated metal enclosure 206, a hollow guide rod 208, a gear rack 210 and a slot 212 for allowing movement of the guide rod 208 and gear rack 210 in the y and z directions.

The arm 190 carries out hydropneumatic aspiration and dispensing functions, and is fitted with an aspiration and dispensing head 216. The aspiration and dispensing head 216 terminates in a tapered metal tip 218 which is used either for aspirating or dispensing controlled amounts of air, or for dispensing system fluid. During aspiration and dispensing operations, the metal tip 218 carries either a disposable pipette tip 134 or one of the pneumatic aspiration and dispensing pipettes 164. A flexible tube 221 passes through the hollow gear rack 202 to allow aspiration and dispensing to be carried out through the metal tip 218. The wash arm 192 is fired with a wash head 194 for a purpose to be described shortly, and a plurality of flexible tubes 214 pass through the hollow guide tube 208 to carry wash fluids to and from the wash head 194.

Since the robotic arms 190 and 192 are, with the exception of the specie components mentioned previously, part of a commercially available apparatus, their construction and operation need not be described in detail. In general, however, the functions of the hydropneumatic aspiration and dispensing arm 190 may be summarized as follows: (a) picking up and ejecting disposable pipette tips 134 and pneumatic aspiration and dispensing pipettes 164, (b) liquid level detection, (c) controlled stepwise movement along the x, y and z axes, and (d) aspiration and dispensing of air and liquids.

Picking up a disposable pipette tip 134 is accomplished by controlling the arm 190 to place the metal tip 218 vertically above one of the disposable pipette tips 134 in the rack 127, and then lowering the head 216 by a predetermined number of steps selected to be below the point at which a disposable pipette tip 134 is engaged. Engagement of the pipette tip 134 displaces a slidable plastic ejector sleeve 228 (best seen in FIGS. 5A–5C) located just above the metal tip 218. By then retracting the head 216 to its home position, which is defined by an electrical contact attached to the upper end of the ejector sleeve 228, the system can determine whether a tip 134 was engaged by comparing the number of steps travelled upwardly and downwardly, which will differ by an amount corresponding to the ejection sleeve displacement. After use, the disposable pipette tips 134 are ejected from the head 216 by the ejector sleeve 228 and are allowed to drop into the slot 148 of the box 144 at the pipette tip disposal station 142. The pipette tip pickup and ejection functions will be described in more detail hereinafter, as will the manner in which the pneumatic aspiration and dispensing pipettes 164 are picked up and released.

The liquid detection function is carried out by selecting an x-y location at which liquid is to be detected (e.g., the location of a sample tube 120 or a reagent bottle 179–182), and then sensing the presence of liquid beginning at a defined position along the z axis by discharging air through the metal tip 218 until the air flow is interrupted by occlusion of the tip. Liquid detection is carried out only with a disposable pipette tip 134 attached to the nozzle 218. After the first liquid detection, which occludes the tip 134 with liquid, subsequent reagent level sensing with the same disposable tip 134 can be carried out empirically by calculating the liquid level based upon the dimensions of the reagent bottle and the amount of reagent removed. In lieu of the airflow method of liquid level detection, a technique based on variations in the electrical capacitance of the metal tip 218 may also be used; this capability is also provided in the above-referenced TECAN system.

Movement of the hydropneumatic aspiration and dispensing head 216 in the x, y and z directions is accomplished by stepping motors (not shown) which are operated under microprocessor control. A software environment known as "Integrator" has been developed by Tecan for this purpose, and is described in three documents entitled 5000/8000 *Series Integrator Software Manual* (Version 7.40, July 1991), *Command Summary* (Version 2.0, Oct. 23, 1989), and *DITI Option Manual* (Document No. 390 542, Version 1.1, October 1992), all of which are incorporated by reference herein. In the preferred embodiment of the present invention, software commands designed for an OS-2 operating system are used and generate outputs which emulate "Integrator" software commands and user interfaces.

Aspiration and dispensing of air and liquids through the metal tip 218 is achieved by means of the fluid supply bottle 46, syringe pump 54 and fluid valve 62 of FIG. 2. The tubing in the system is primed with system fluid, which can either be dispensed directly or used as a hydraulic fluid medium for aspirating or dispensing measured amounts of air through the metal tip 218. The syringe pump 54 is driven automatically by a stepping motor under microprocessor control, and the valve 62 is also controlled automatically by a solenoid to either fill the syringe 54 from the supply bottle 46 or to aspirate or dispense air or liquid through the metal tip 218, depending upon the position of the valve 62.

As noted above, the wash arm 192 is generally similar in construction to the hydropneumatic aspiration and dispensing arm 190, except that the wash head 194 is installed in place of the hydropneumatic aspiration and dispensing head 216. The functions of the wash arm 192 are as follows: (a) controlled stepwise movement along the x, y and z axes, (b) dispensing of wash fluid into the assay devices 90, and (c) aspiration of wash fluid and reagents from the assay devices 90.

Movement of the wash head 192 along the x, y and z axes is carried out by stepper motors under microprocessor control, in the same manner as the hydropneumatic aspiration and dispensing arm 190. Software commands control the speed and position of the wash head 194 at each moment during the operating cycle, with the movements of the wash arm 192 being coordinated and synchronized with those of the hydropneumatic aspiration and dispensing arm 190.

Dispensing of wash fluid into the assay devices 90 is carried out automatically by drawing wash fluid from the supply bottle 48 of FIG. 2 and dispensing it through nozzles at the wash head 194. As will be described in more detail hereinafter, the wash head 194 has three separate nozzles for dispensing wash fluid, with one nozzle being aligned with each well of a given assay device 90. There is a separate syringe pump 56, 58 and 60 in FIG. 2 for each of the wash head dispensing nozzles, and the fluid control valves 64-1 through 64-3 of FIG. 2 connect the syringes either to the supply bottle 48 (to fill the syringes) or to the dispensing nozzles at the wash head 194. As in the case of the hydropneumatic aspiration and dispensing head 216, the syringes 56–60 which supply the dispensing nozzles of the wash head 194 are controlled automatically by stepper motors to deliver predetermined amounts of wash fluid at controlled rates. The fluid control valves 64-1 through 64-3 are also controlled automatically, with the position of the valves being the same for each of the three syringes 56–60 at any given time.

Aspiration of wash fluid and liquid reagents from the wells of the assay devices 90 is carried out by providing the wash head 194 with a second set of nozzles which are used only for aspiration. These nozzles are connected by flexible tubes to pumps 222, visible in FIG. 3, which are switched on and off automatically at the appropriate times under computer control.

Additional features of the reaction area 66 of the cabinet 22 will be evident from FIG. 3, in which a rear panel has been removed from the reaction area 66 to illustrate components that are not visible in FIG. 2. A circuit board 224 mounted vertically on a rear wall of the cabinet 22 carries electrical drivers for the heating platens 92, 94 and 100 at the reaction stations 78–84. The circuit board 224 is connected by wires (not shown) to the electrical heating elements and to platinum RTD (resistance temperature device) temperature sensors located in the heating platens 92, 94 and 100. A temperature controller (not shown) controls the duty cycle of the electrical power provided to the heating elements, so that the temperature at each of the platens 92, 94 and 100 can be precisely regulated. In the preferred embodiment, separate temperature feedback loops are provided for the assay device heating platens 94 at each of the reaction stations 78–84, but the lower and upper reaction device heating platens 92 and 100 at each reaction station are controlled by a common feedback loop. A suitable multiple-loop temperature controller for use in the present invention is the ANAFAZE BCLS Loop System, which is available from ANAFAZE, Inc. of Watsonville, Calif. Alternatively, a multiple-loop controller described in a commonly-assigned, copending U.S. patent application of Gene A. Benton, Ser. No. 08/177,829, filed on Jan. 5, 1994 and incorporated herein by reference, may be used. The heating platens 92, 94 and 100 are conventional resistance heating laminates, approximately 1/16 inch in thickness, and are available commercially from Watlow of St. Louis, Mo. Thermal fuses (not shown) are provided to protect the heating platens 92, 94 and 100 against overheating. Also visible in FIG. 3 are four cooling fans 226 which are installed on an elevated shelf at the rear of the cabinet 22, immediately behind the rear edge of the locator plate 76. As will be described in more detail hereinafter, these fans draw air from a plenum located below the reaction stations 78–84 in order to hasten the cooling of the reaction device heating platens 92 at each reaction station after power is removed from these platens.

As shown in the exploded view of FIG. 4, many of the components of the reaction area 66 are removable from the locator plate 76 or deck 77 by the operator. These include the trays 86, the sample tube rack 110, the disposable pipette tip rack 127, the pipette tip disposal container 144, the wash cup 156 and the reagent bottle holder 166. This is advantageous not only in facilitating the introduction and removal of samples and expendable supplies by laboratory personnel, as described earlier, but also in allowing the locator plate 76 or deck 77 to be cleaned. If desired, the design of the cabinet 22 may be modified by eliminating the locator plate 76 and placing all locating devices directly on the deck 77, thereby providing a smoother surface to facilitate routine cleaning and containment of spilled liquids.

Figure 5A:
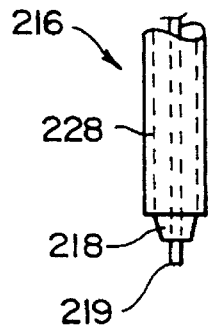
FIGS. 5A–5C are detailed views illustrating the manner in which a disposable pipette tip is picked up and ejected by one of the robotic arms.
Figure 5B:
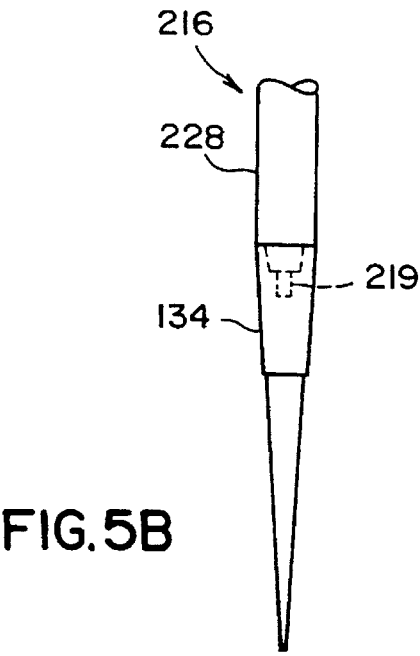
Figure 5C:
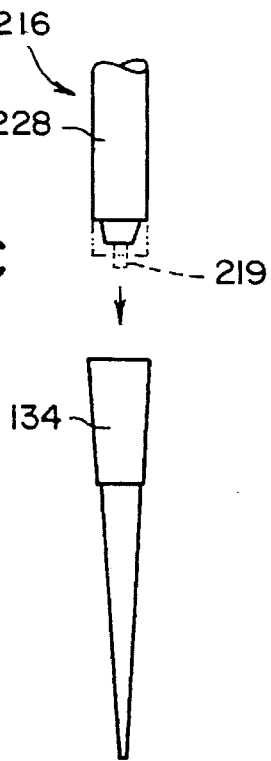

FIGS. 5A through 5C illustrate the manner in which a disposable pipette tip 134 is picked up and ejected by the hydropneumatic aspiration and dispensing head 216. In FIG. 5A, the lower portion of the pneumatic aspiration and dispensing head 216 is shown without a disposable pipette tip in place. The metal tip 218 extends downwardly by a short distance beyond the lower edge of a slidable plastic ejector sleeve 228, and carries a small-diameter tube or nozzle 219 through which air or system fluid is aspirated or dispensed. In order to pick up a disposable pipette tip 134, the head 216 is lowered in order to force the nozzle 218 (which is slightly conical and beveled at its lower end as shown) into frictional engagement with the opening or lumen at the upper end of the disposable tip 134. This is possible since the disposable pipette 134 is held against downward movement by the rack 127 of FIG. 3. With the head 216 and disposable pipette tip 134 thus joined, the combined structure can be used for aspirating and dispensing liquids (i.e., liquid biological samples and reagents) by drawing or discharging precisely controlled amounts of air through the nozzle 219. This is done by controlling the syringe pump 54 of FIG. 2 to displace a corresponding amount of system fluid in the tube connecting the syringe 54 and nozzle 219, while maintaining a volume of air (rather than system fluid) at the end of the tube which adjoins the nozzle 219. When it is desired to eject the disposable pipette tip 134 into the disposal container 144 of FIGS. 3 and 4, the robotic arm 190 of FIG. 3 is moved to the upper limit of its z-direction travel, causing the upper end of the sleeve 228 (not shown in FIGS. 5A–5C) to strike a fixed stop or obstruction. This has the effect of displacing the sleeve 288 in a downward direction, against a spring force, as illustrated in FIG. 5C. This causes the disposable tip 134 to separate from the nozzle 218 and to fall by gravity into the slot 148 of the disposal container 144. When the robotic arm 190 again moves downwardly from the upper limit of its z-direction travel, the upper end of the sleeve 228 separates from the stop and the lower end of the sleeve returns to the position shown in FIG. 5A. The tip ejection function using the slidable ejector sleeve 228 is a standard feature of the TECAN system referred to previously, but the illustrated metal tip 218 and nozzle 219 represent modifications made to the TECAN system for the purposes of the present invention. These modifications will be described in more detail hereinafter.

Figure 6A:
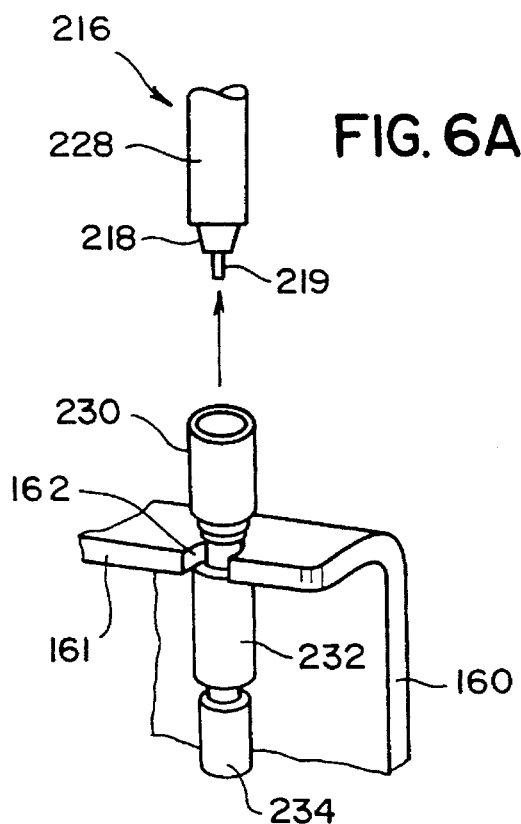
FIGS. 6A and 6B are detailed views illustrating the manner in which a pneumatic aspiration and dispensing pipette is picked up and released by the robotic arm of FIGS. 5A–5C.
Figure 6B:
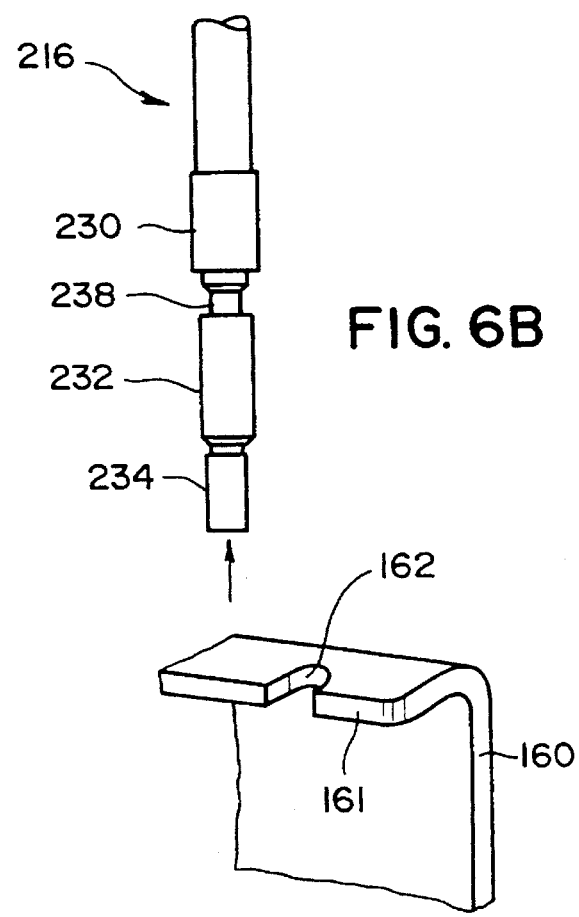

FIGS. 6A and 6B illustrate the manner in which the head 216 picks up and releases one of the two pneumatic aspiration and dispensing pipettes 164 of FIG. 3. The construction of the pneumatic aspiration and dispensing pipettes 164 is disclosed in more detail in the aforementioned copending U.S. patent application of Allen S. Reichler et al, filed on even date herewith and entitled "Nucleic Acid Amplification Method and Apparatus" (Attorney's file 2573-P1), which is incorporated herein by reference. Briefly, the pneumatic aspiration and dispensing pipette 64 includes a rigid, generally cylindrical plastic portion 230 which is attached at its lower end to a resilient tip 234 made of silicone rubber or the like. The resilient tip 234 is formed with a hole (not shown) on its lower face which communicates with the lumen 236 of the plastic portion 230, and is adapted to be brought into contact with a pneumatic port on each of the reaction devices 88 of FIG. 4 in order to control the movement of a liquid sample within the reaction device. When the pneumatic aspiration and dispensing pipette 164 is not in use, it is held on the bracket 160 of FIGS. 3 and 4 by virtue of the engagement between a restricted or narrowed area 238 of the plastic portion 230 and one of the U-shaped notches or cut-outs 162 in the upper horizontal lip or flange 161 of the bracket 160. When it is desired to use the pipette 164 to carry out pneumatic aspiration or dispensing on one of the reaction devices 88, the robotic arm 190 is controlled to bring the metal tip 218 on the pneumatic aspiration and dispensing head 216 into alignment with the lumen 236 of the pipette 164 as shown in FIG. 6A. The head 216 is then moved downwardly to bring the tip 218 into frictional engagement with the lumen 236, thereby coupling the head 216 with the pipette 164. This is followed by a horizontal movement of the head 216 in the y direction to disengage the pipette 164 from the cut-out 162, and then by an upward movement in the z direction to clear the bracket 160. The resulting positions of the head 216, pipette 164 and bracket 160 are illustrated in FIG. 6B. At this point, the pipette 164 can be moved into contact with the pneumatic port of one of the reaction devices 88 by appropriate movements of the robotic arm 190, and used to aspirate air from or dispense air into the reaction device by automatically controlling the syringe pump 54 of FIG. 2 in the manner described previously. When it is desired to return the pipette 164 to the bracket 160, the robotic arm 190 is controlled to maneuver the narrowed or restricted area 238 of the pipette 164 into horizontal alignment with one of the notches 162 in the bracket 160. A further horizontal movement of the head 216 in the y direction brings the pipette 164 into engagement with the notch 162 of the bracket 160, and a subsequent upward movement of the head 216 in the z direction separates the nozzle 218 from the lumen 236 of the pipette 164. This returns the components to the positions shown in FIG. 6A, whereupon the pneumatic aspiration and dispensing head 216 is free to perform other functions.

As shown in FIGS. 3 and 4, the bracket 160 preferably holds two pneumatic aspiration and dispensing pipettes 164. This provides redundancy in case one of the pipettes 164 becomes dislodged from the bracket 160 and cannot be picked up by the robotic arm 190. The robotic arm 190 is capable of detecting whether a pipette 164 has been engaged, in the same way as described previously in connection with the disposable pipette tips 134. If the first pipette 164 cannot be engaged, the control system is programmed to move to the location of the second pipette 164 and to engage that pipette as a backup.

Figure 7A:
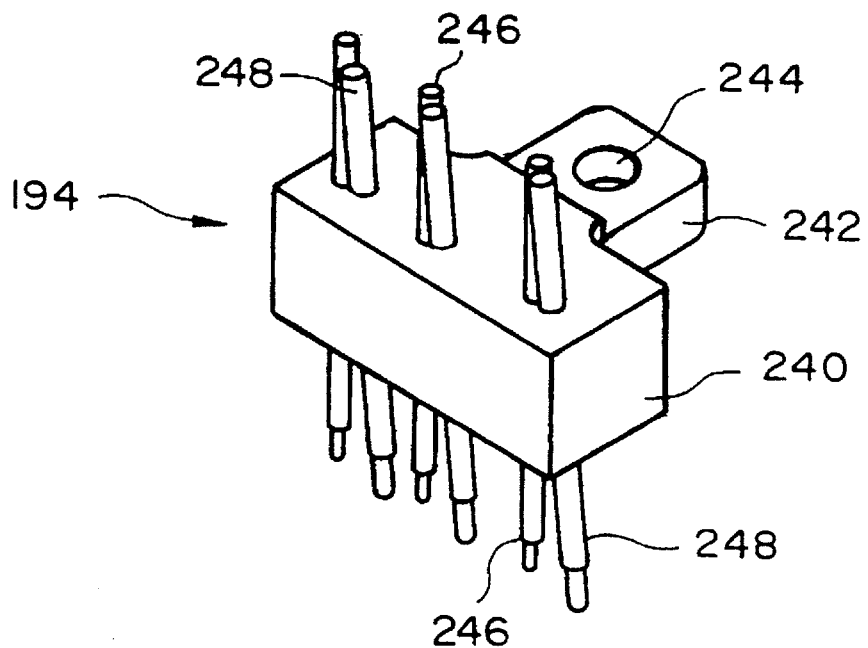
FIGS. 7A and 7B are detailed perspective and side views of a wash head that is provided on a second robotic arm for dispensing and aspirating wash fluid.
Figure 7B:
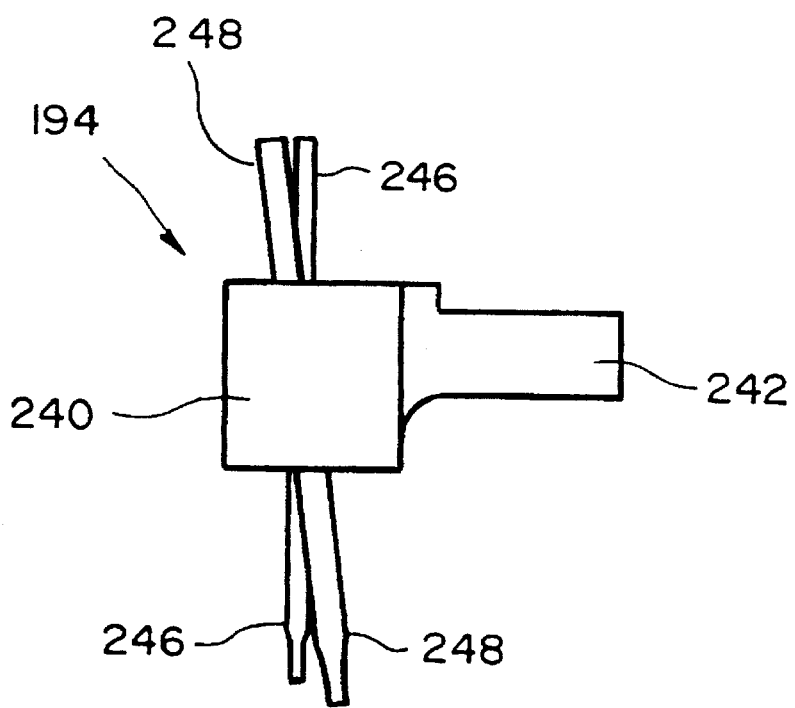

FIGS. 7A and 7B are enlarged views of the wash head 194 that is carried by the wash arm 192 of FIG. 3. The flexible tubes 214 of FIG. 3 have not been shown in FIGS. 7A and 7B for clarity. The wash head 194 comprises a solid, generally rectangular body 240 of plastic material, such as polyvinylchloride (PVC), with a rear extension 242 that permits attachment to the rack 210 of the wash arm 192 by means of an aperture 244. Holes are formed through the main portion of the plastic body 240 to tightly receive two sets of rigid metal tubes or conduits 246 and 248. The conduits 246 extend vertically through the plastic body 240, while the conduits 248 extend at a compound angle of approximately 10° from the vertical when viewed from the end of the plastic body 240 in FIG. 7B and approximately 41° from the vertical when viewed from the front of the plastic body in FIG. 7A. The conduits 246 are used for dispensing wash fluid into the wells of the assay devices 90, while the conduits 248 are used to aspirate reagents and wash fluid from the wells of the assay devices 90. The diameter of the aspiration conduits 248 is larger than the diameter of the dispensing conduits 246, and the aspiration conduits 248 extend slightly lower than the dispensing conduits 246 as illustrated in FIG. 7B. The lowermost ends of both sets of conduits 246 and 248 are crimped or narrowed, as shown, to form nozzles. Preferably, an adhesive is used to bond the conduits 246 and 248 to the holes in the plastic body 240.

As will be described in more detail in connection with FIGS. 14R and 14S, the wash head 194 is lowered by the wash arm 192 of FIG. 3 so that the lower (nozzle) ends of the conduits 246 and 248 are received in the wells of the assay devices 90, with each well receiving the lower ends of a respective pair of conduits 246 and 248 simultaneously. To this end, the spacing between the lower ends of each pair of conduits 246 and 248 is such that both conduits are receivable within the diameter of an assay device well. Depending upon the function being carried out by the wash head 194, fluid is either dispensed from the conduits 246 or aspirated into the conduits 248 at any given time. Although not illustrated in FIGS. 7A and 7B, the flexible tubes 214 of FIG. 3 are attached to the upper ends of the conduits 246 and 248, in the area adjoining the upper surface of the plastic body 240. One set of flexible tubes delivers wash fluid to the dispensing conduits 246 from the supply bottle 48 and syringes 56–60, and the other set of flexible tubes couples the aspiration conduits 248 to the pumps 222 and waste bottle 32 of FIG. 1. The length and flexibility of the flexible tubes 214 is sufficient to allow for the desired range of movement of the wash arm 192 of FIG. 3.

Figure 8A:
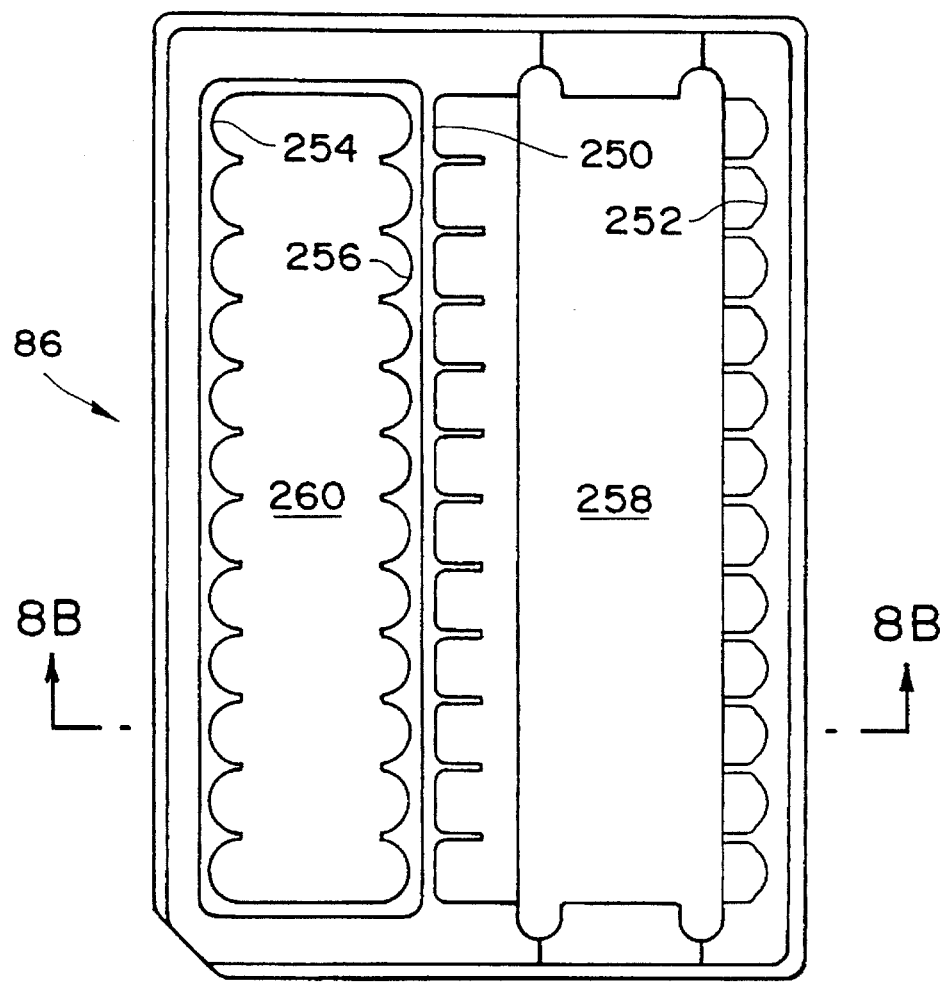
FIGS. 8A and 8B are detailed top plan and sectional views, respectively, of one of the removable trays shown in FIGS. 3 and 4.
Figure 8B:
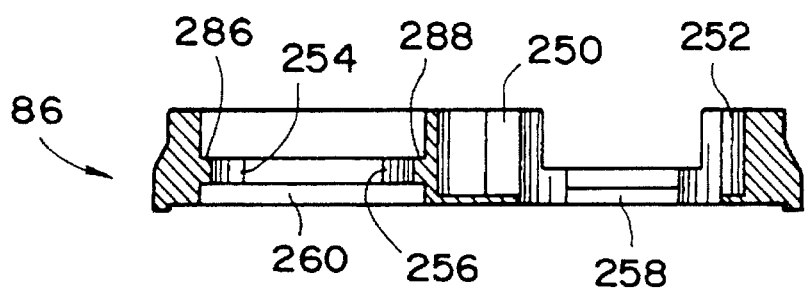

FIGS. 8A and 8B are top plan and side sectional views, respectively, of one of the removable trays 86 shown in FIGS. 3 and 4. The purpose of the tray 86 is to hold a plurality of reaction devices 88 and assay devices 90 for convenient handling by laboratory personnel, and to locate these devices at predetermined positions at the reaction stations 78–84. To this end, the tray 86 is formed with two opposed rows of slots or cavities 250 and 252 which are shaped to receive the ends of the reaction devices 88, and with two opposed rows of slots or cavities 254 and 256 which are shaped to receive the ends of the assay devices 90. In the illustrated embodiment, the tray 86 accommodates twelve reaction devices 88 and twelve assay devices 90, with each assay device 90 received at a position adjacent to a corresponding one of the reaction devices 88. Cut-out portions 258 and 260 are formed in the bottom of the tray for allowing the bottom surfaces of the reactions devices 88 and assay devices 90 to make direct contact with the respective heating platens 92 and 94 of FIGS. 3 and 4. The tray 86 is preferably made from a suitable heat-resistant plastic material, such as Delrin or Ultem 1000.

Figure 9A:
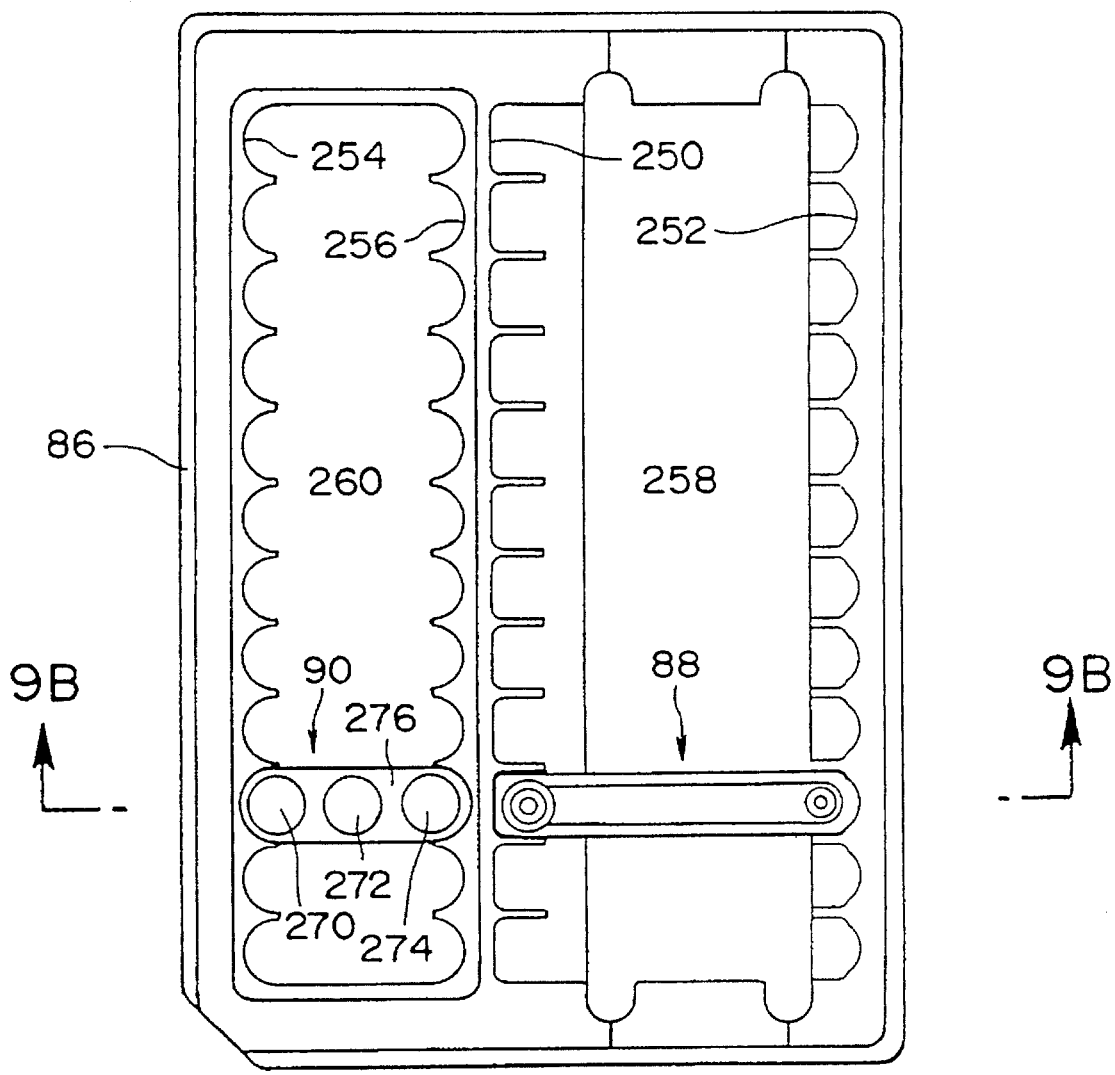
FIGS. 9A and 9B are detailed top plan and sectional views similar to those of FIGS. 8A and 8B, with a reaction device and an assay device shown in the removable tray.
Figure 9B:
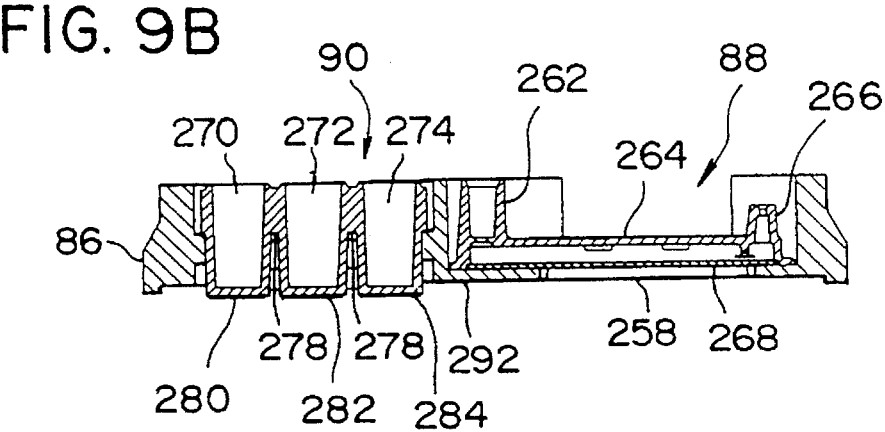

FIGS. 9A and 9B are plan and sectional views similar to FIGS. 8A and 8B, but with one reaction device 88 and its corresponding assay device 90 shown in position within the tray 86. It will be understood that, although only one reaction device 88 and one assay device 90 are shown in FIGS. 9A and 9B, the tray 86 will normally be filled with as many reaction devices 88 and assay devices 90 as there are samples to be assayed at the corresponding reaction station 78-84. Each reaction device 88 includes a sample tower 262 through which liquid biological samples are introduced, an elongated rectangular body portion 264 through which the sample is moved during the decontamination and amplification reactions, and a pneumatic tower 266 through which pneumatic aspiration and dispensing is carried out in order to move the sample within the body portion 264. The reaction device 88 has a substantially flat bottom surface 268, a portion of which (corresponding to the locations of the decontamination and amplification areas within the body portion 264) is exposed through the cut-out 258 at the bottom of the tray 86.

The assay device 90 comprises three connected microwells 270, 272 and 274 which are generally cylindrical in configuration, with their side walls tapering slightly inward from top to bottom to produce a frusto-conical shape. The interior walls of the sample wells are coated with a dried capture reagent (typically biotinilated BSA/Streptavidin) for use during the nucleic acid assay. The microwells 270, 272 and 274 are connected to each other by means of a generally planar, horizontal flange 276 extending between and parallel to the open tops of the microwells, and by vertical webs 278 which are formed between adjacent wells immediately below the flange 276. Each of the microwells 270, 272 or 274 has a substantially flat bottom surface 280, 282 or 284. As illustrated in FIG. 8B, the slots or cavities 254 and 256 of the tray 86 which support the assay devices 90 are formed with upwardly-facing ledges 286 and 288 which are engaged by a notch or step 290 that is formed around the perimeter of the assay device 90. As a result of this arrangement, the assay device 90 is supported at a predetermined vertical positions within the tray 86 and are held against downward movement. This position is such that the flat bottom surfaces 280–284 of the microwells 270–274 extend slightly below the bottom surface 292 of the tray 86, as shown in FIG. 9B.

Figure 10A:
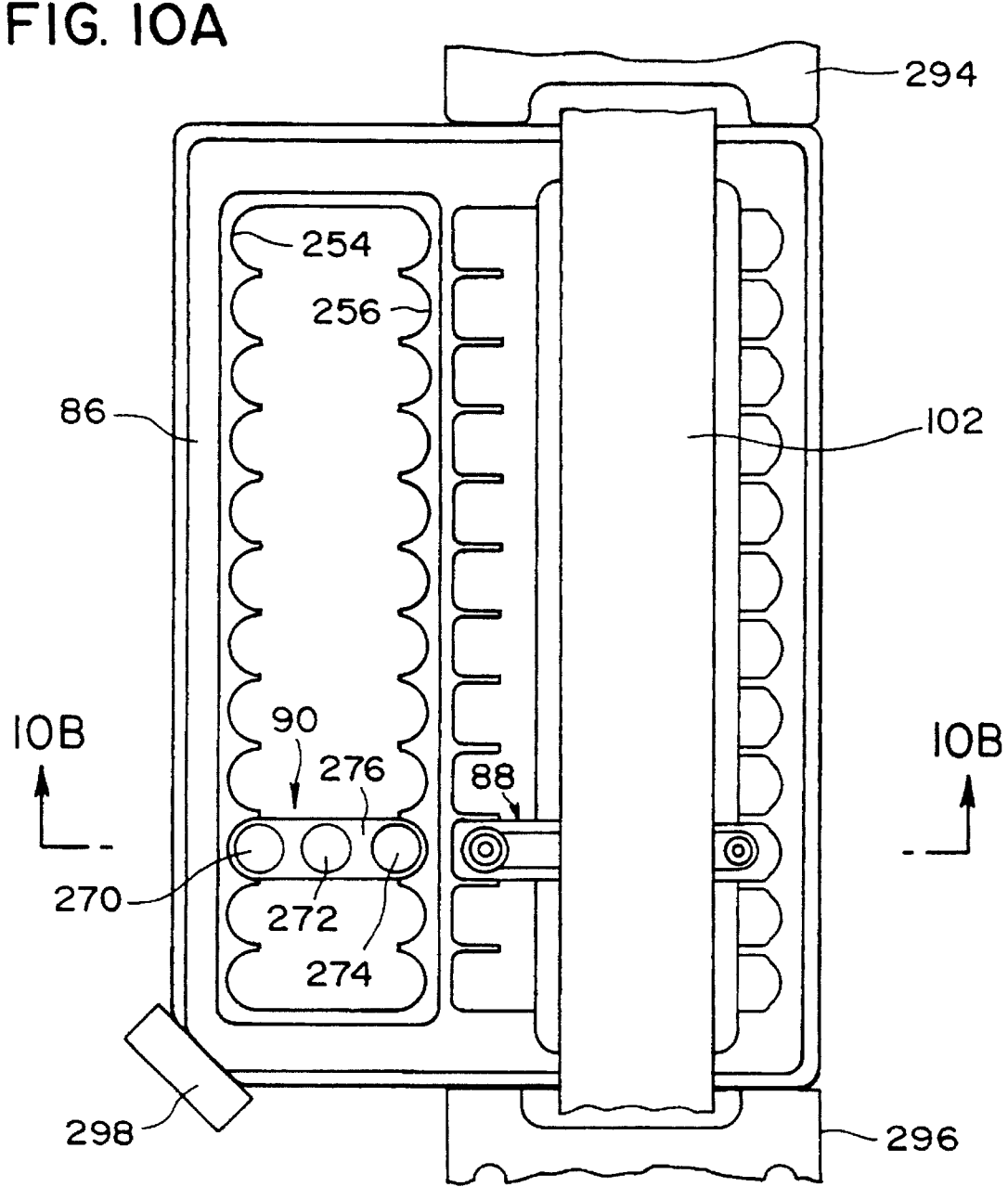
FIGS. 10A and 10B are detailed top plan and sectional views similar to those of FIGS. 9A and 9B, with the removable tray shown in position at one of the reaction stations of FIGS. 2–4.
Figure 10B:
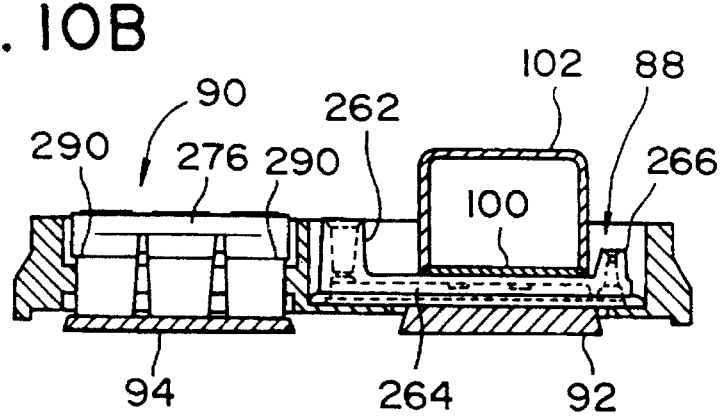

FIGS. 10A and 10B are plan and sectional views similar to FIGS. 9A and 9B, showing the tray 86 in place at one of the reaction stations 78–84 of FIGS. 3 and 4. The pivotable arm 102 is shown in the closed position, with the U-shaped clamp 106 of FIGS. 3 and 4 serving to lock the arm 102 in this position and to compress the body portion 264 of the reaction device 88 between the heating platens 92 and 110. This provides efficient heat transfer from the heating platens 92 and 110 to the liquid biological sample contained within the reaction device 88. As shown in FIG. 10B, the interior of the arm 102 is substantially hollow (except for stiffening ribs that are not visible in the drawing); this provides thermal insulation between the platen 100 and the top surface of the arm 102 and thus protects the operator against exposure to high temperatures.

The flat bottom surfaces 280–284 of the microwells 270–274 of the assay device 90 are brought into contact with the upper surface of the heating platen 94 when the tray 86 is installed at the reaction station. As this occurs, the assay device 90 is lifted slightly in the tray 86, causing the peripheral notch or step 290 to separate from the ledges 286 and 288. By allowing the assay device to "float" in the tray 86 in this manner, good thermal contact between the bottom surfaces 280–284 of the assay devices 90 and the upper surface of the heating platen 94 is assured.

As illustrated in FIG. 10A, the tray 86 is held in a predetermined position and orientation at the reaction station by means of three locating devices 294, 296 and 298. The locating device 294 is a plate-like structure that affixes the rear hinge 104 of the arm 102 to the deck 76, as shown in FIG. 4, and the locating device 296 is a similar plate-like structure that affixes the U-shaped clamp 106 to the deck 76. The locating devices 294 and 296 make contact with opposite ends of the tray 86 in order to properly locate the tray at the reaction station. The third locating device 298 is in the form of a diagonal block which is affixed to the deck 76, and which makes contact with the forward left-hand corner of the tray 86. As illustrated, the forward left-hand corner of the tray 86 is angled or beveled in such a manner as to conform to the angle of the block 298. In this way, the tray 86 has only one possible orientation at the reaction station and cannot inadvertently be installed incorrectly. This insures that the reaction devices 88 and assay devices 90 proper make contact with their respective heating platens 92 and 94.

FIGS. 11A and 11B are a perspective views illustrating two alternative embodiments of the assay devices 90. In the embodiment of FIG. 11A, the assay devices 90 are manufactured in strips 300 of four, with each assay device 90 being connected to the next by means of a narrow web or tab 302 extending from the upper flange 276. The webs or tabs are formed on alternating sides of the strip 300 from one assay device 90 to the next. The assay devices 90 are preferably made of a molded plastic material, such as polystyrene, with the tabs 302 integrally formed using the same material. The individual assay devices 90 are easily separated from each other by bending or twisting the strip 300 to break the tabs 302. In the embodiment of FIG. 11B, the assay devices 90 are formed individually, rather than in strips; this produces more uniform edges around the assay devices 90 since the tabs 302 are no longer required. In both embodiments, the assay devices are formed with thin bottom walls (preferably about 0.022 inch in thickness) to promote efficient heating of the liquid samples, and are preferably white in color with a high pigment content to enhance fight collection and reduce cross-talk during the chemiluminescent detection step. The horizontal flange 276 and webs 278 which connects the three microwells 270–274 of each assay device 90 are advantageous in that they resist bowing of the assay device and thus maintain the flat bottoms 280–284 of the microwells in a parallel, coplanar relationship, so that proper contact with the heating platen 94 can be achieved.

FIG. 12 is a cross-sectional view illustrating the internal details of one of the reaction devices 88. The reaction device 88 is disclosed in more detail in the aforementioned copending patent application of Allen S. Reichier et al, entitled "Nucleic Acid Amplification Method and Apparatus", which is incorporated herein by reference. The sample tower 262 of the reaction device 88 is provided with a sample port 304 through which a liquid biological sample (not shown) is introduced. The sample passes through an aperture 306 at the bottom of the sample tower, and is received in a sample area 308 in the form of a liquid bolus. The pneumatic tower 266 at the opposite end of the reaction device 88 includes a pneumatic port 310 through which pneumatic aspiration and dispensing is carried out in order to move the liquid bolus horizontally within the reaction device 88. Initially, air is aspirated through the pneumatic port 310 to cause the liquid sample to move from the sample area 308 to the decontamination zone 312 of the reaction area 314, where the sample makes contact with dried decontamination reagents 316. After a suitable incubation time, during which heat is applied to the reaction area 314 by the heating platens 92 and 100 of FIG. 10B, further aspiration through the pneumatic port 310 causes the liquid sample to move from the decontamination zone 312 to the amplification zone 318. In the amplification zone 318, the liquid sample contacts dried amplification reagents 320 and undergoes a nucleic amplification reaction. A suitable incubation period is provided for the amplification reaction, and heat is applied to the reaction area 314 by the heating platens 92 and 100 during this interval. The heat is then increased for a short period of time to provide a heat spike that terminates the amplification reaction. Following completion of the amplification reaction, air is dispensed into the pneumatic port 310 to cause the liquid sample to move from the amplification zone 318 through the decontamination zone 312 and back to the sample area 308. The liquid sample is then withdrawn from the reaction device 88 by inserting a pipette 134 (not shown) through the sample port 304 and orifice 306.

Figure 13:
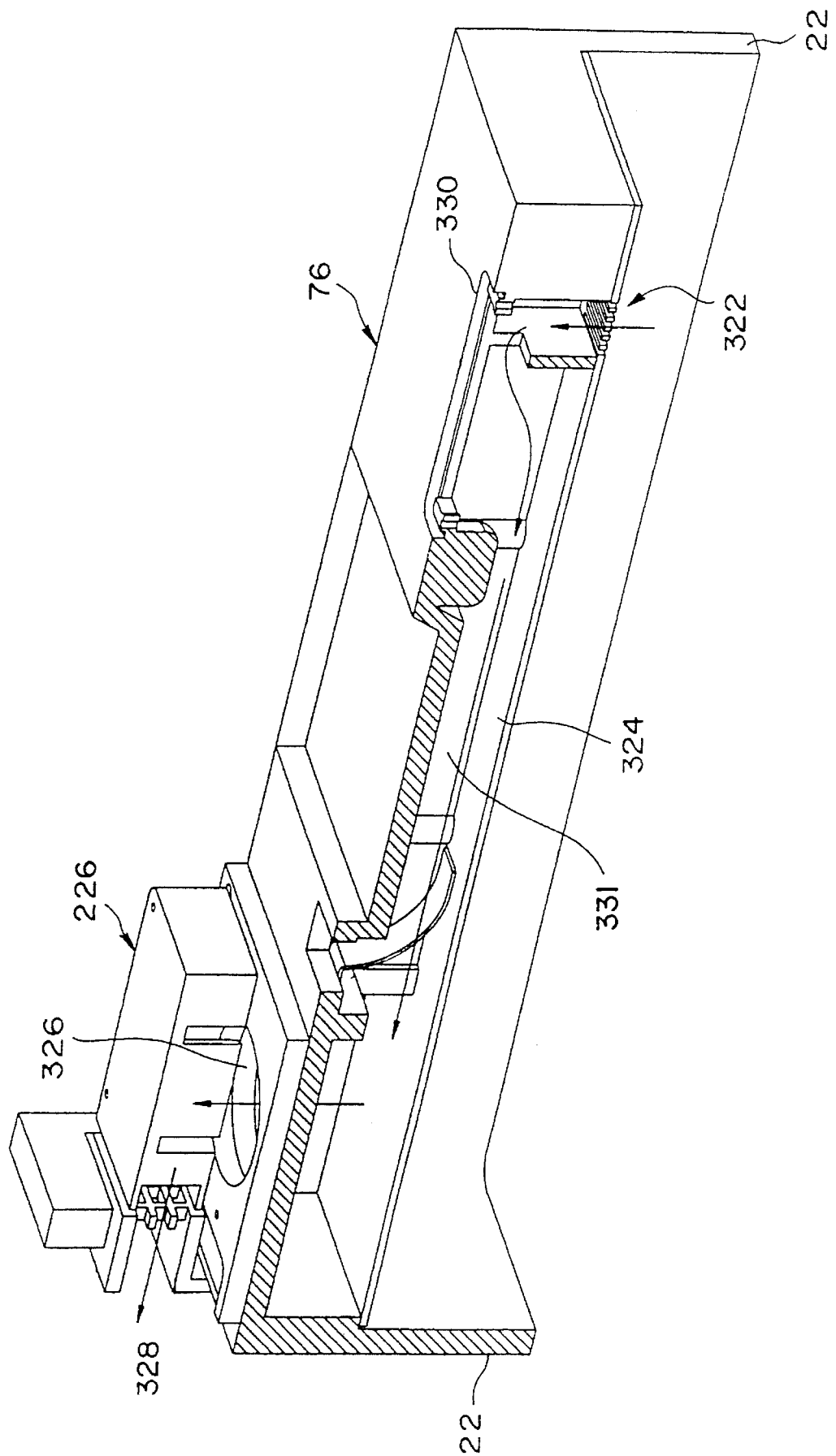
FIG. 13 is a cross-sectional view of the lower portion of the cabinet shown in FIGS. 1–4, illustrating the arrangement used for cooling the reaction device heating platens during intervals when these heating platens are deactivated.

FIG. 13 is a partial cross-sectional view through the deck 76 of FIG. 3, illustrating a cooling arrangement for the reaction device heating platens 92 and 94. For clarity, the components which are normally mounted on the deck 76 have been removed in FIG. 13, and the portions of the cabinet 22 above the level of the deck 76 have also been removed. Beneath the forward edge of the cabinet 22, an air inlet 322 communicates with a baffled plenum chamber 324 located below the deck 76. At the rear of the cabinet 22, the plenum chamber 324 communicates with an aperture 326 on which one of the fans 226 of FIG. 3 is mounted. The fan 226 draws air from the plenum chamber 324 through the aperture 326, and exhausts the air through an air outlet 328 located at the rear of the cabinet 22. In this way, a continuous circulation of air is maintained in the plenum chamber 324. At the forward end of the plenum chamber 324, immediately above and behind the air inlet 322, a cut-out is provided for receiving one of the heating platens 92 of FIGS. 3 and 4. Similar cut-outs are provided for the heating platens 92 of the remaining reaction stations. When power is removed from the heating platens 92 following the heat spike referred to earlier, the circulation of air in the plenum chamber 324 provides a cooling effect which allows the heating platens 92 to reach ambient temperature more quickly. In this way, more rapid temperature transitions can be obtained in the reaction devices 88. Baffles 331 divide the plenum chamber 324 into channels extending from front to rear beneath the deck 76, in order to confine the cooling air flow to the reaction device heating platens 92 and to isolate the air flow from the assay device heating platens 94, the latter operating at lower temperatures and not requiring an air flow for cooling.

Figure 14A:
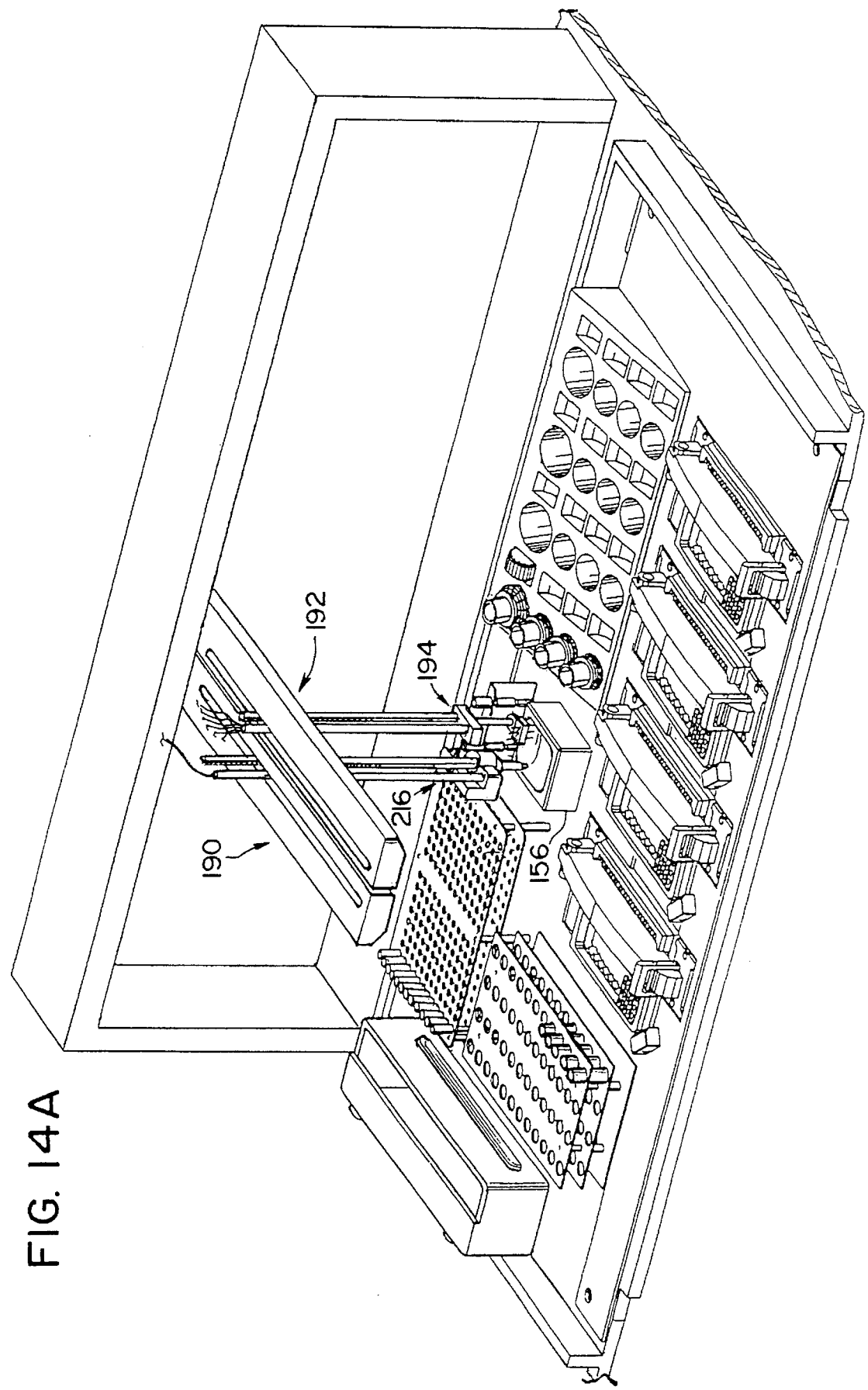
FIGS. 14A–14T are sequence views illustrating the programmed sequence of movements executed by the two robotic arms of FIG. 3 during an automated nucleic acid assay.
Figure 14B:
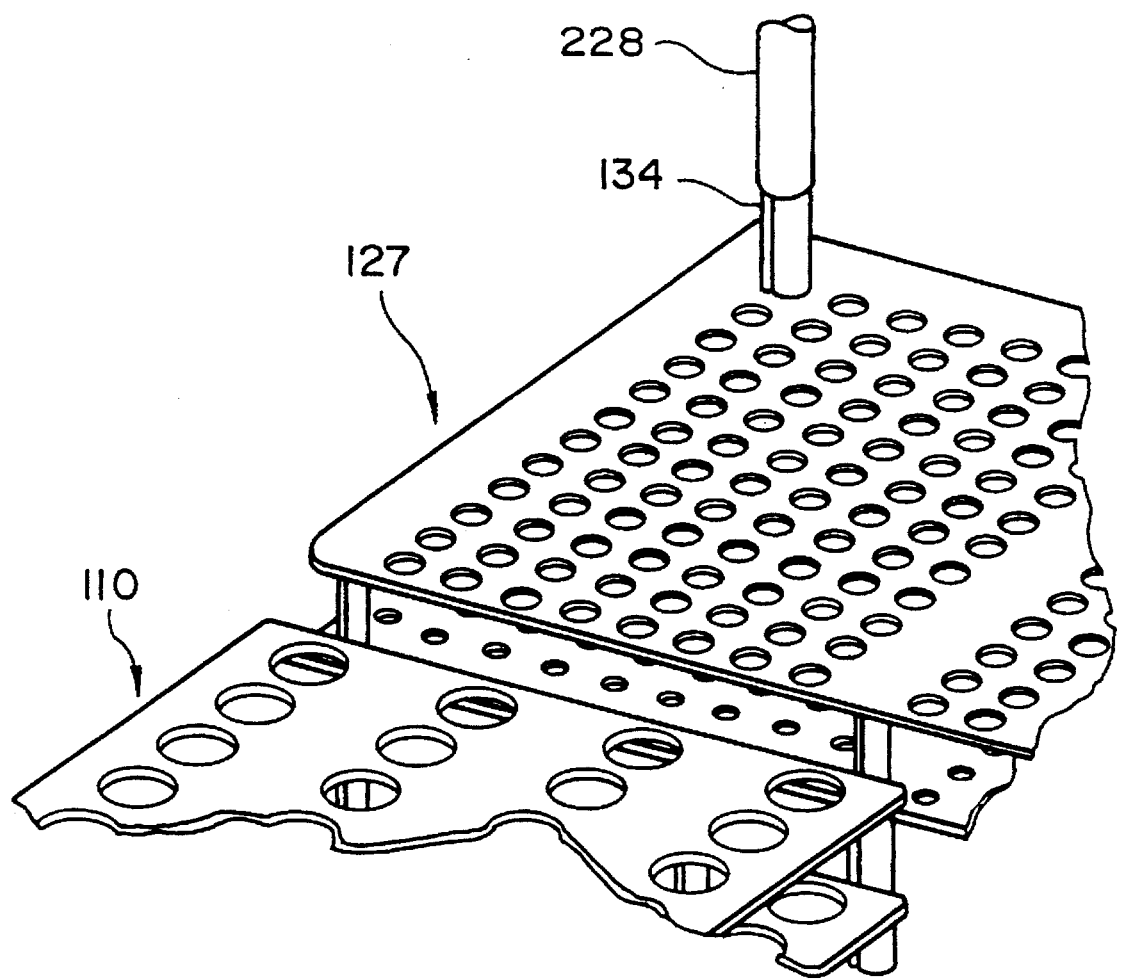
Figure 14C:
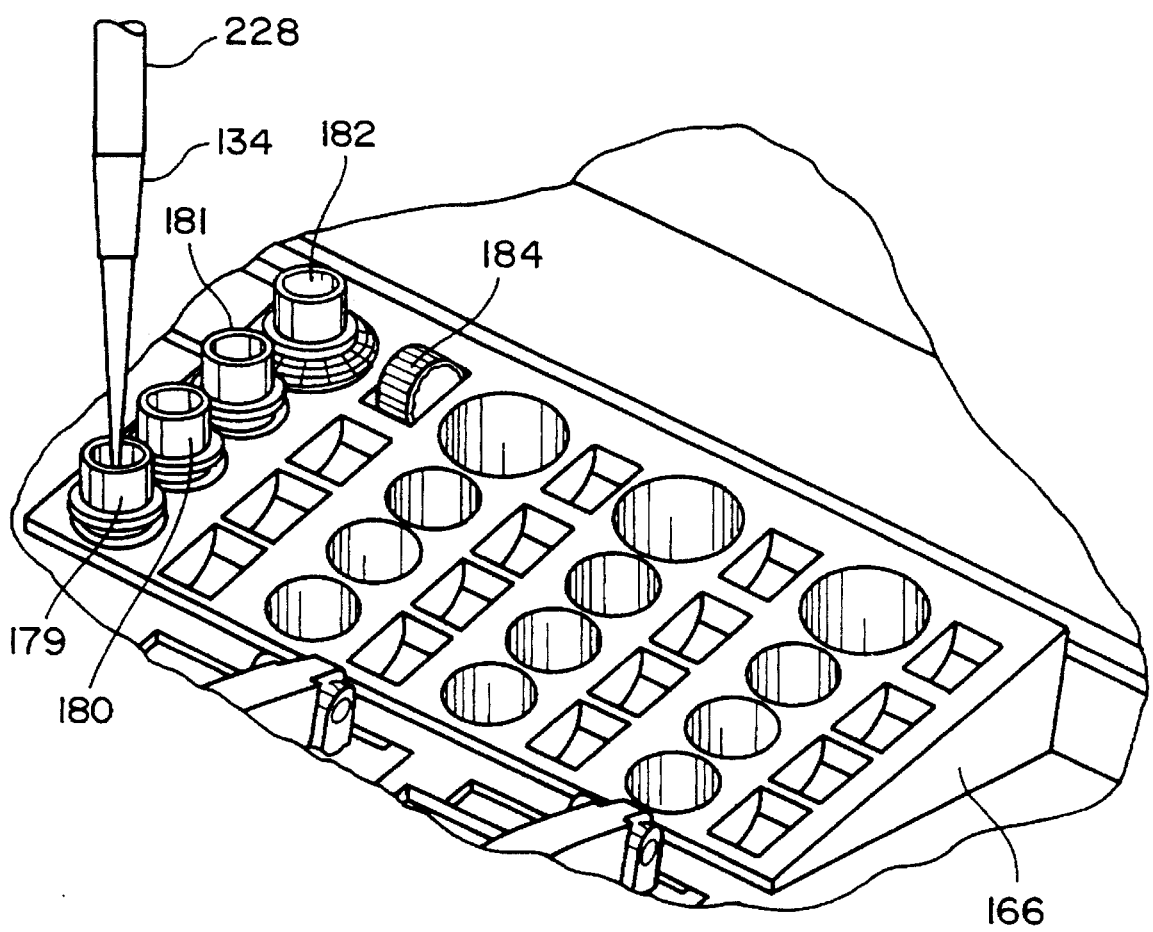
Figure 14D:
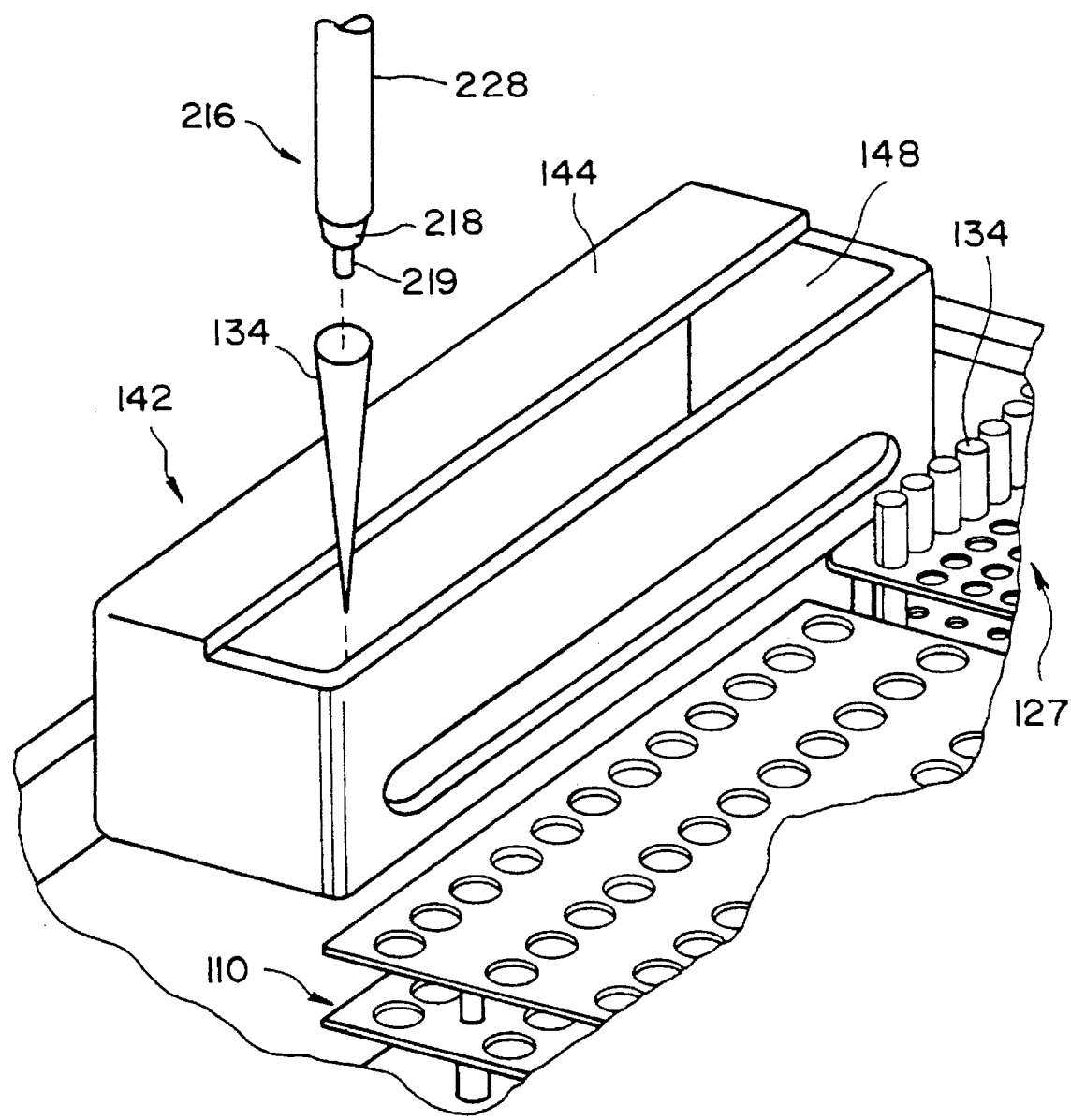
Figure 14E:
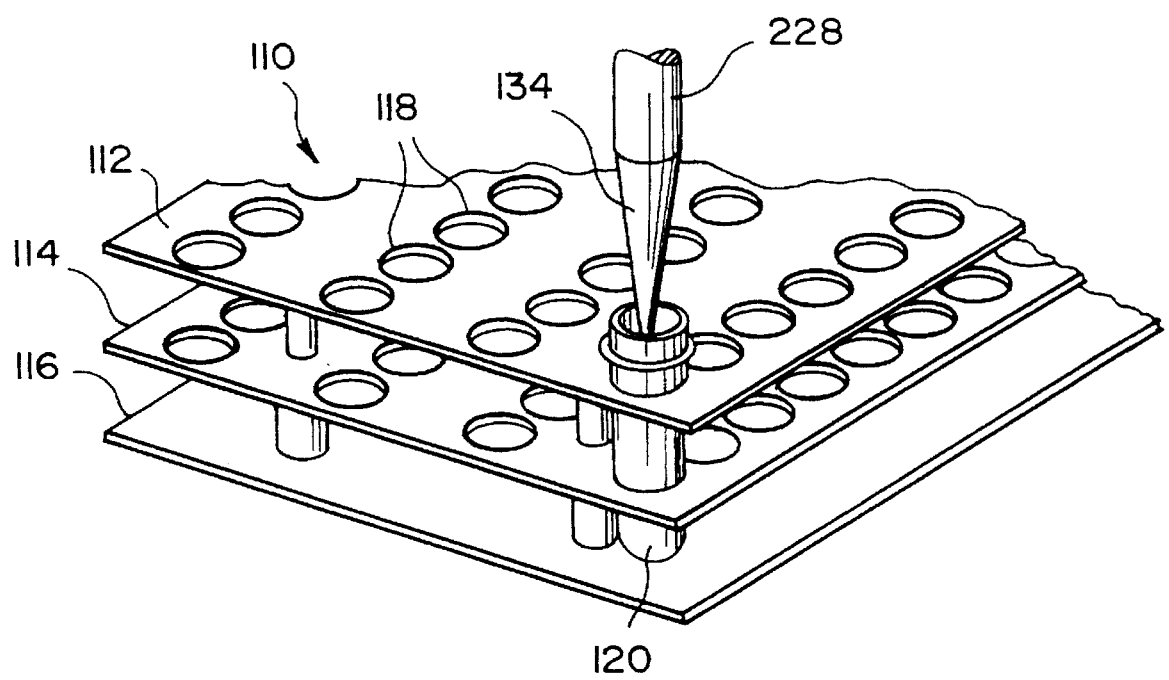
Figure 14F:
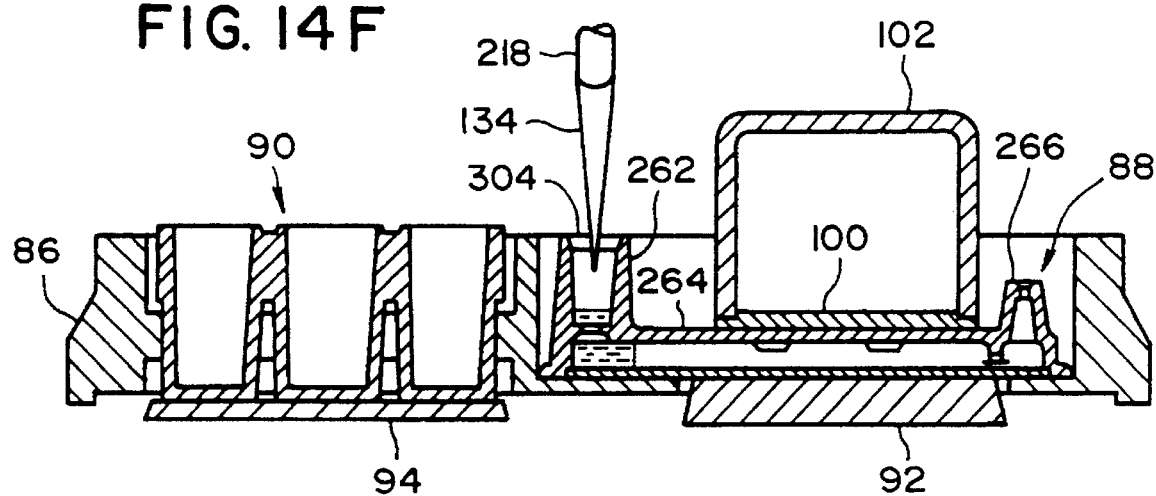
Figure 14G:
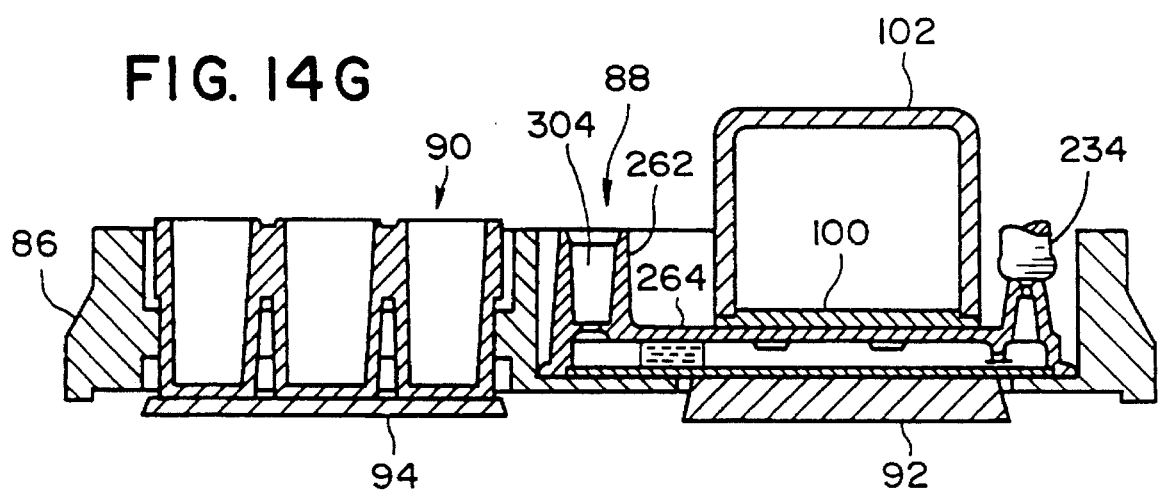
Figure 14H:
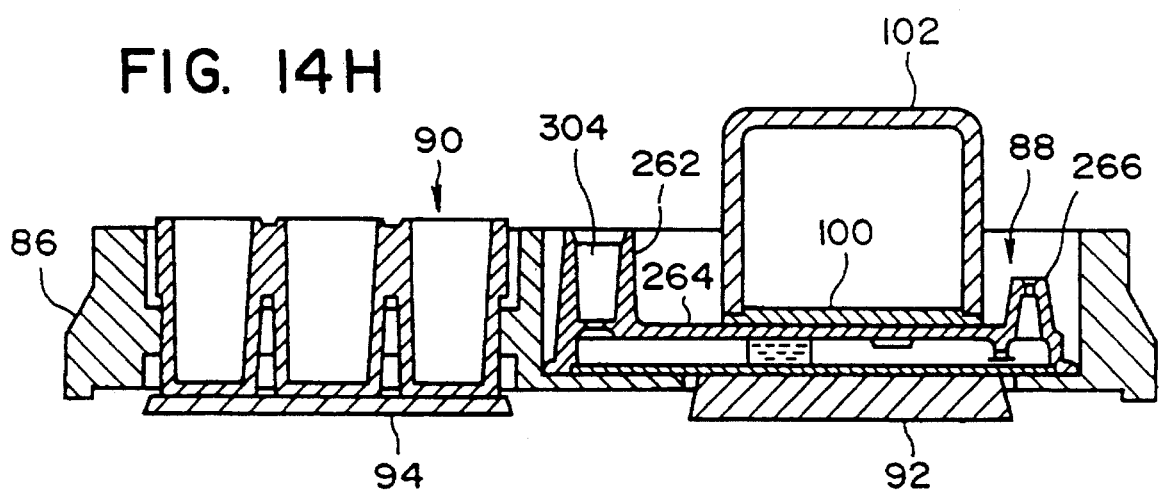
Figure 14L:
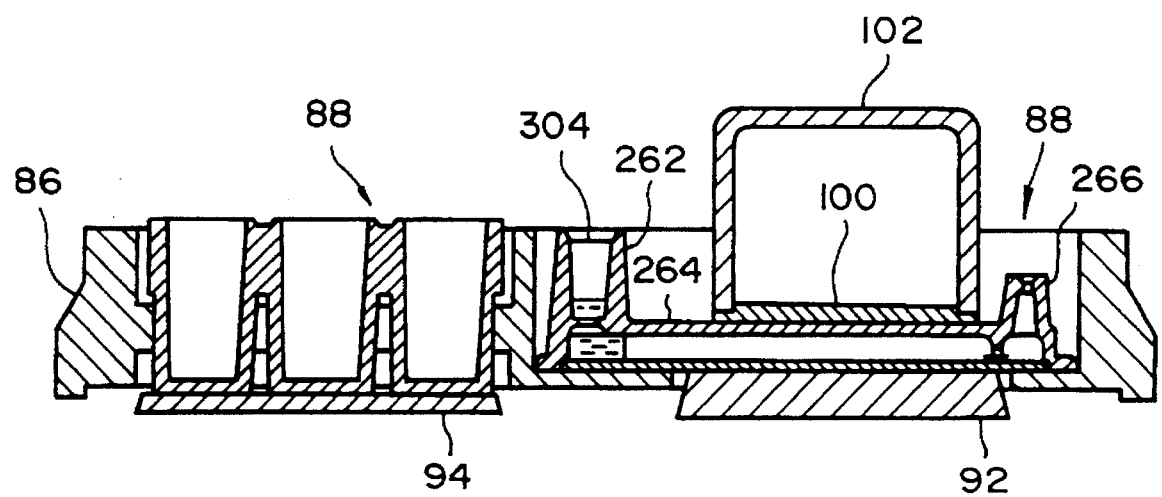
Figure 14M:
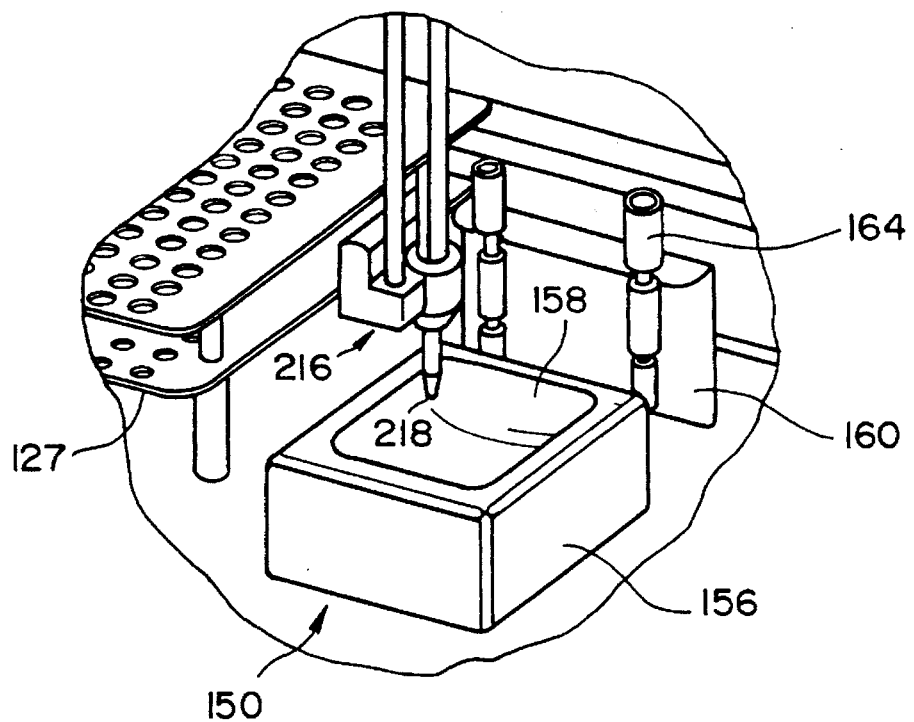
Figure 14N:
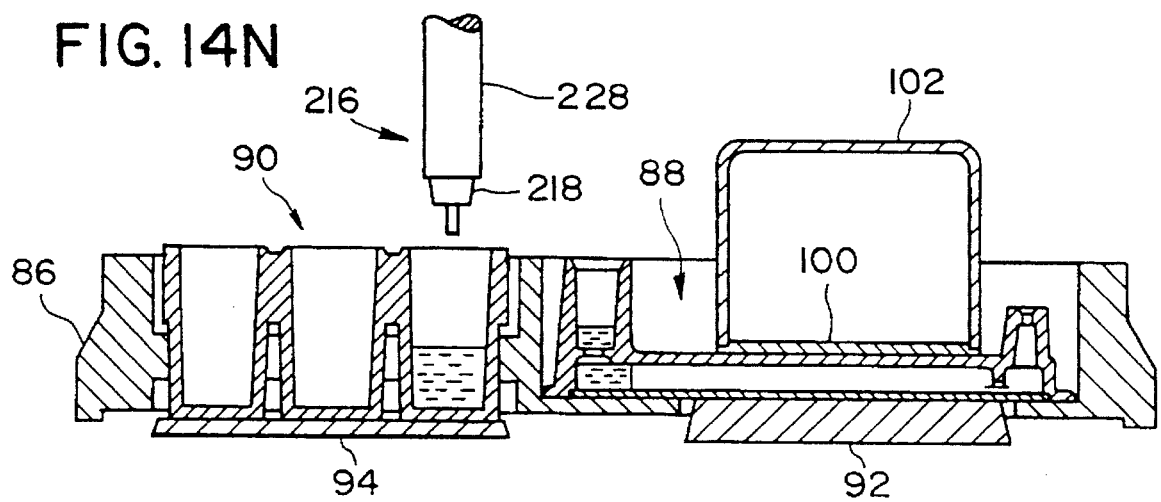
Figure 14O:
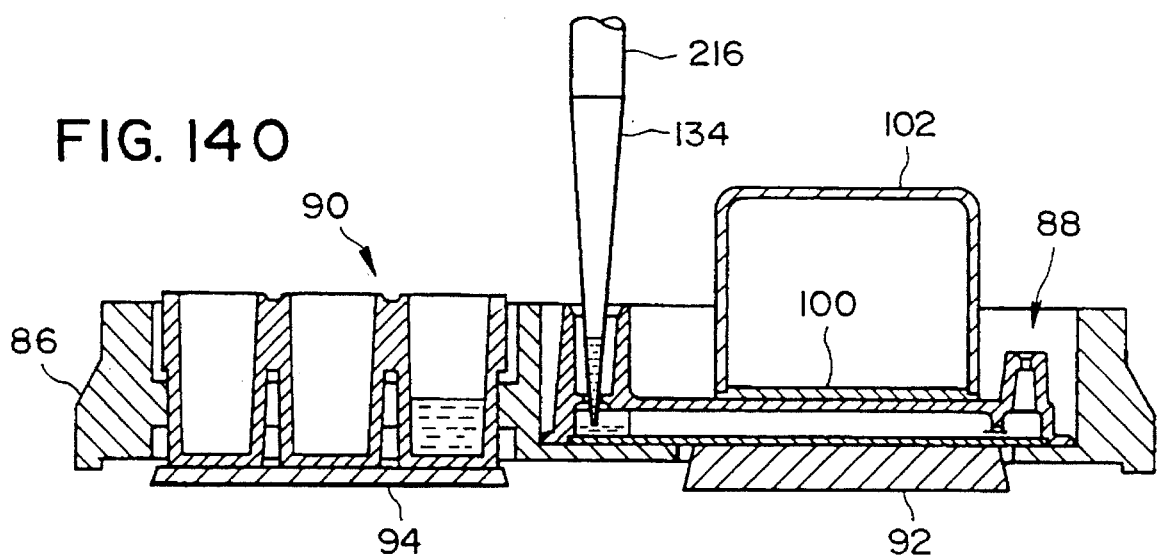
Figure 14P:
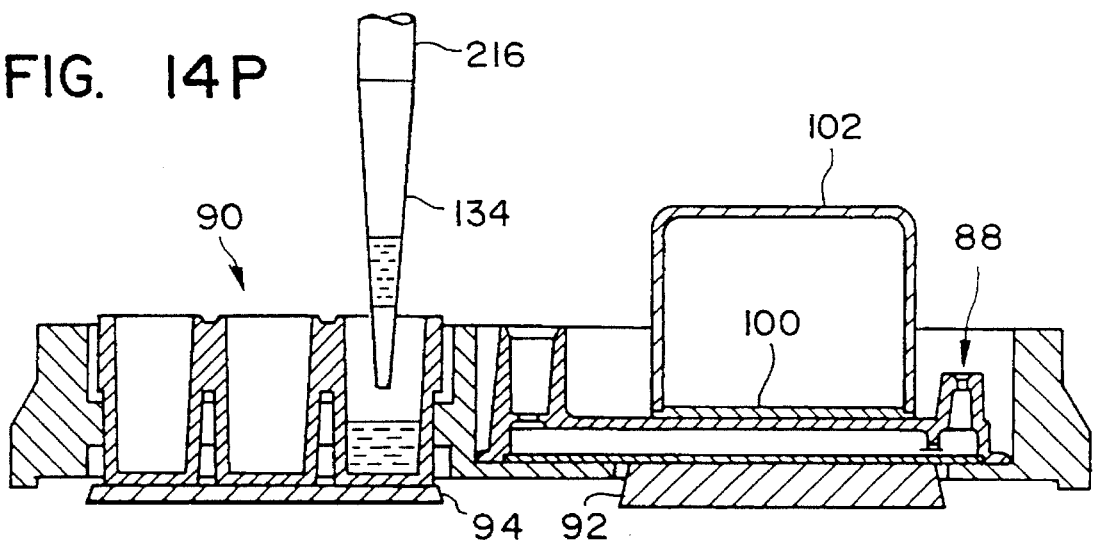
Figure 14Q:
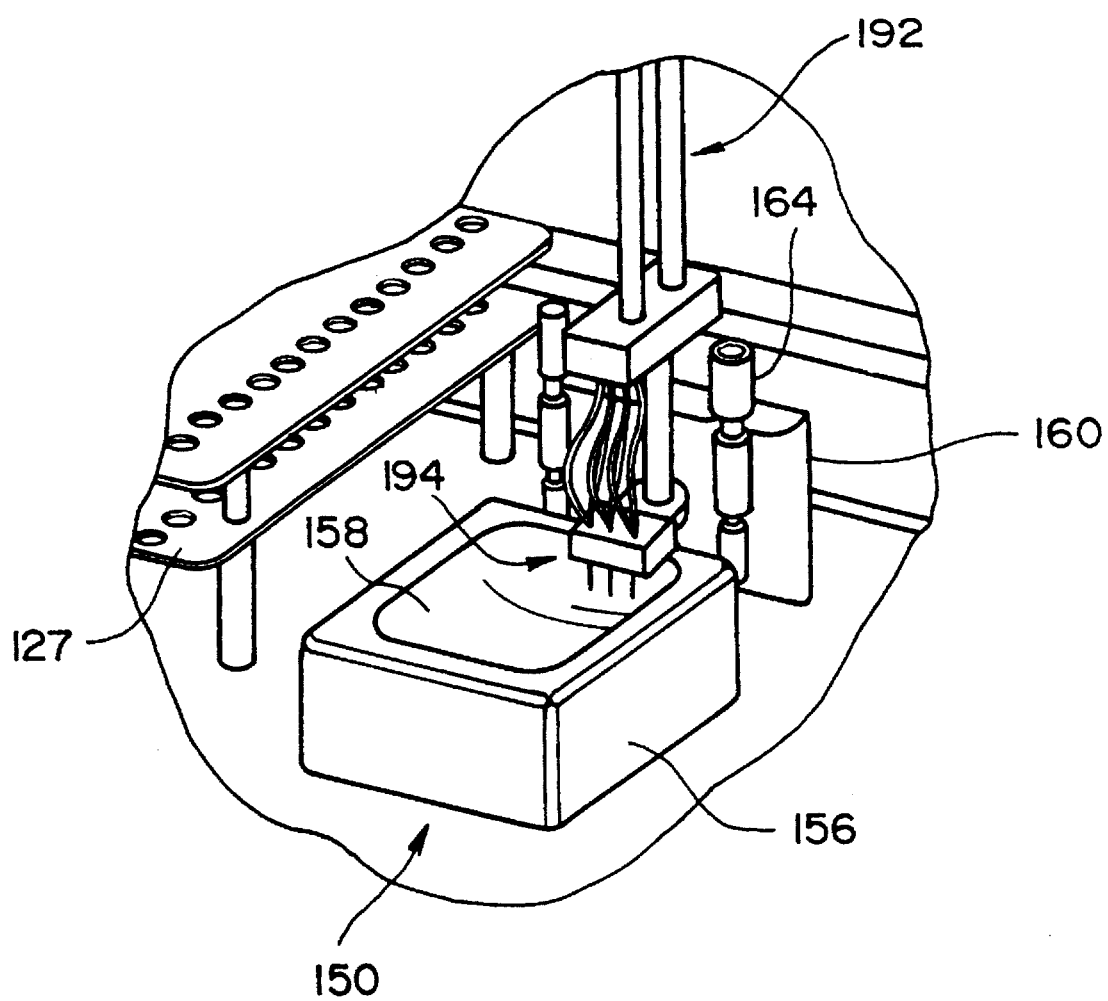
Figure 14R:
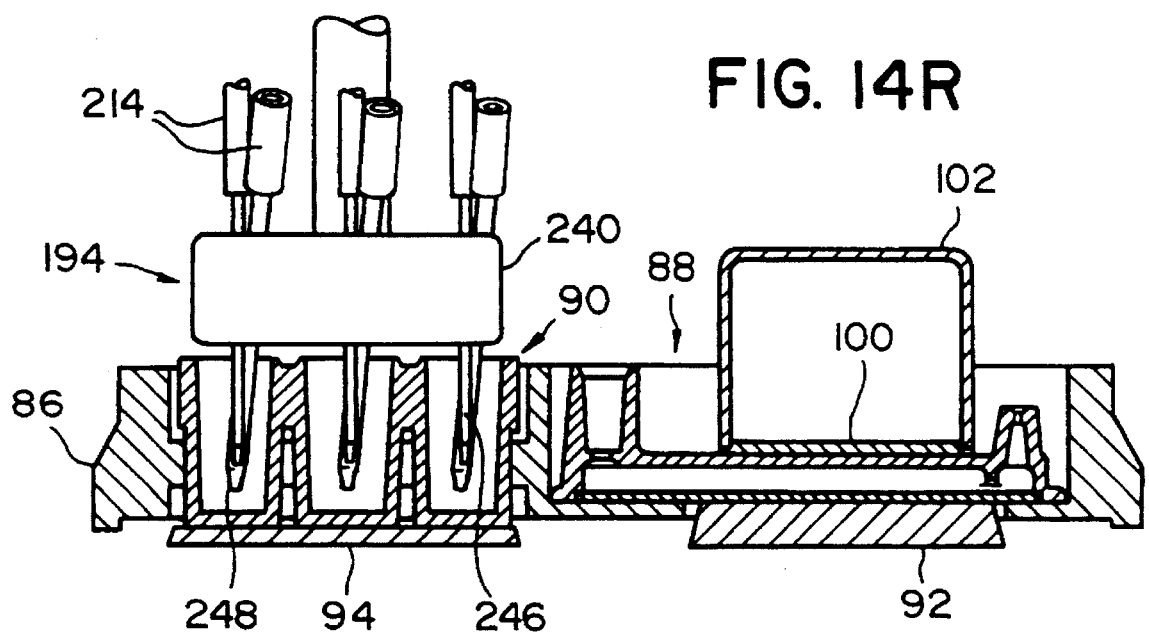
Figure 14S:
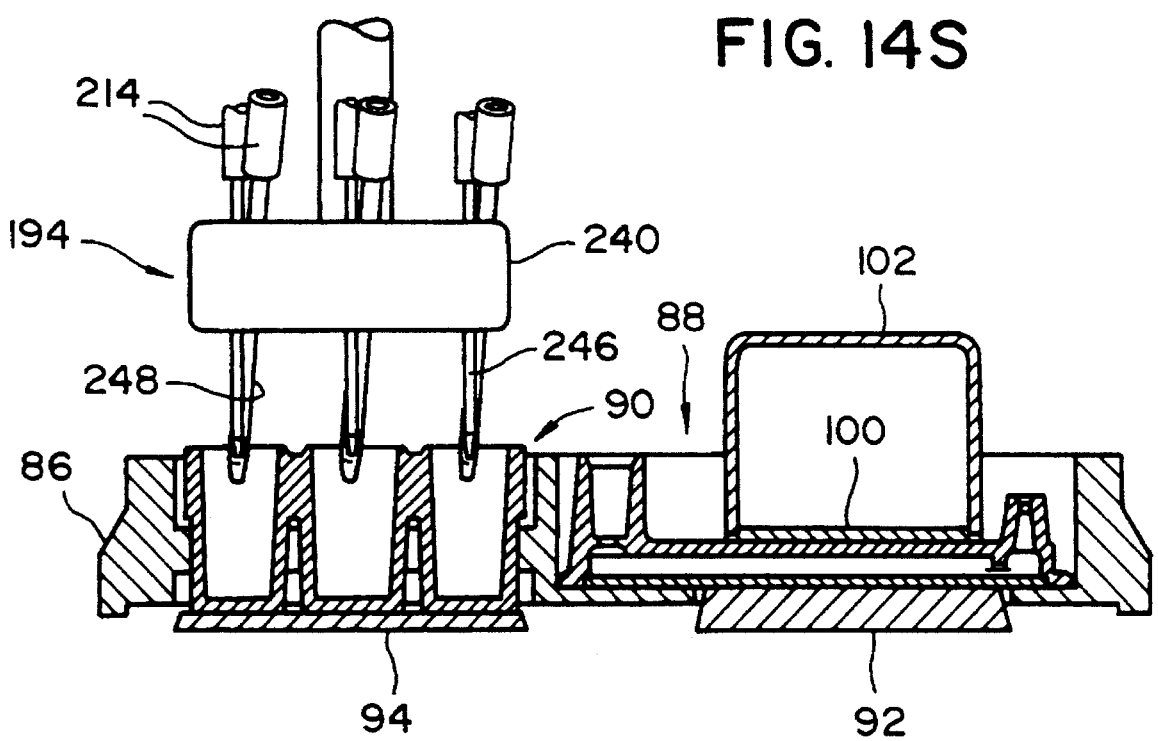
Figure 14T:
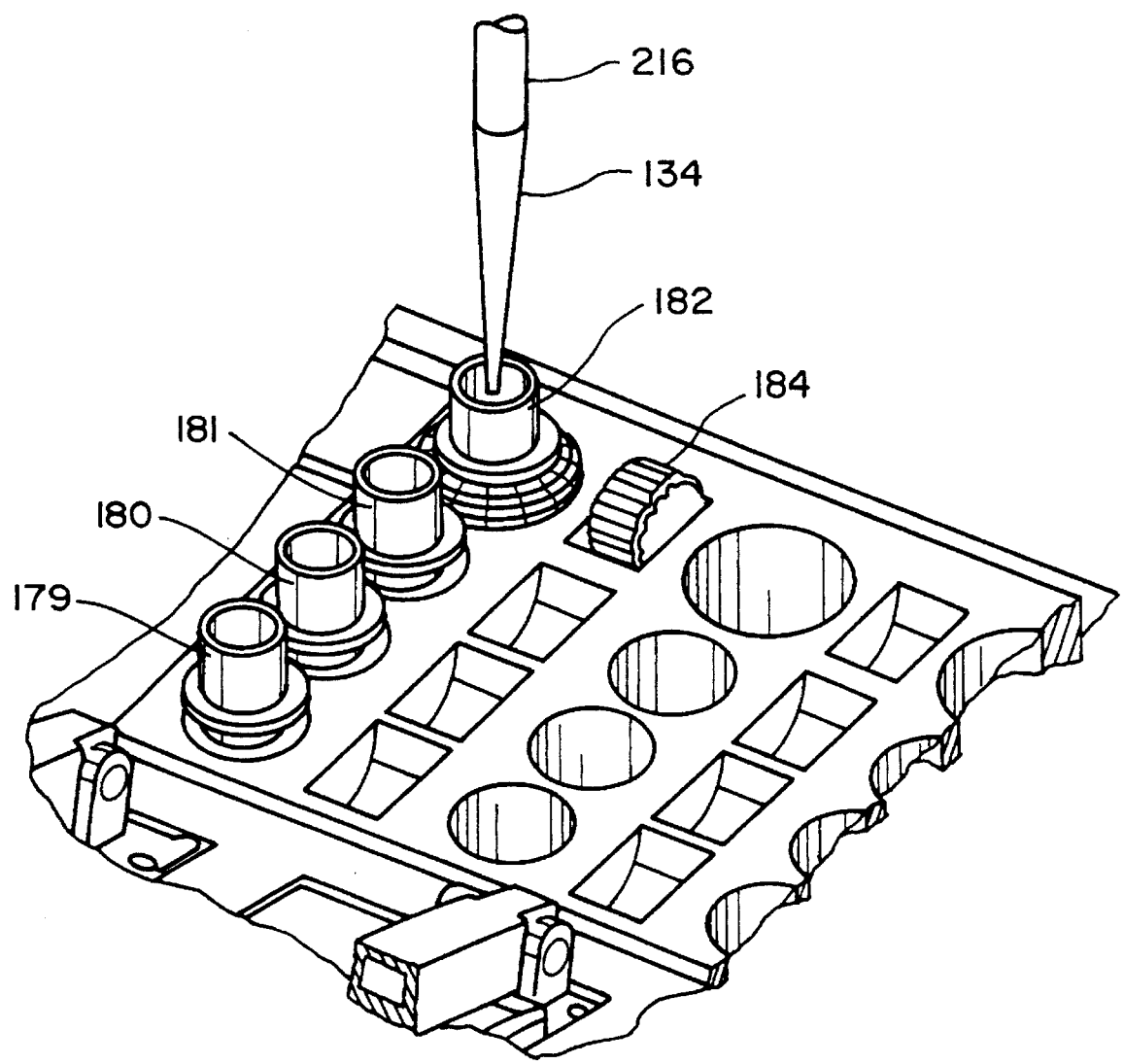

FIGS. 14A–14T are a series of sequence views illustrating the programmed series of movements carried out by the robotic arms 190 and 192 during the course of a nucleic acid assay. Prior to the start of the assay, the trays 86 are loaded with the desired number of reaction devices 88 and assay devices 90, with both types of devices being equal in number and loaded at adjacent positions in the tray 86. Preferably, the trays 86 are sequentially loaded (without empty slots) and are fully loaded except for the last tray used, which may have unoccupied slots depending upon the total number of samples and controls to be assayed. The trays 86 are filled from front to back beginning with the first reaction station 78 and ending with the last reaction station 84. Filled reagent bottles 179–182 are placed into the left-hand row of cavities in the reagent holder 166, with their caps removed and placed in the adjacent cavities 178. The three smaller reagent bottles 179–181 contain hybridization reagents of different specificity which are used during the nucleic acid assay, and the larger reagent bottle 182 contains a chemiluminescent reagent such as Lumi-Phos 530 (a trademark of Lumigen Inc. Southfield, Mich.). The disposable pipette rack 127 is also installed with a supply of disposable pipette tips 134 in place. Preferably, the rack 127 is completely filled with disposable pipette tips 134 to insure that an adequate supply of tips will be available. Finally, the sample tube rack 110 is installed and is provided with sample tubes 120 containing the liquid biological samples to be assayed. The first sample tube 120 occupies the right front aperture 118 of the sample rack 110, and subsequent sample tubes 120 are loaded from front to back. Before commencing the assay, the fluid supply bottles 46 and 48 of FIG. 2 are checked to insure that there is an adequate supply of system fluid and wash solution.

The assay is commenced by sending an appropriate command to the system computer through the keyboard 36 of FIG. 1. As the first step in the process, the robotic arms 190 and 192 move from their home positions (shown in FIG. 3) to positions above the wash cup 156 as shown in FIG. 14A. Air is then purged from the pneumatic aspiration and dispensing head 216 by dispensing a small amount of system fluid from the nozzle 218, and the dispensing nozzles 246 of the wash head 194 are purged in a similar manner. Fluids discharged by the hydropneumatic aspiration and dispensing head 216 and wash head 194 are collected by the wash cup 156 and are then aspirated by the aspiration nozzles 248 of the wash head 194.

In FIG. 14B, the robotic arm 190 moves the hydropneumatic aspiration and dispensing head 216 to a position above the disposable pipette tip rack 127 and picks up one of the disposable pipette tips 134. The first tip 134 to be picked up is at the rear left-hand corner of the rack 127, and subsequent tips are picked up from back to front.

In FIG. 14C, the robotic arm 190 maneuvers the hydropneumatic aspiration and dispensing head 216 (now carrying a disposable pipette tip 134) to a position above the lowermost reagent bottle 179. The disposable pipette tip 134 is then lowered into the reagent bottle 179 while the hydropneumatic aspiration and dispensing head 216 is operated in the liquid detection mode. This allows the reagent level in the bottle 179 to be detected, so that a warning can be produced on the video monitor 38 of FIG. 1 in the event that an insufficient quantity of reagent remains for the desired number of assays.

In FIG. 14D, the robotic arm 190 moves the hydropneumatic aspiration and dispensing head 216 to a position above the pipette tip disposal station 142, and the used pipette tip 134 is ejected into the slot 148 of the box 144. This completes the liquid level check for the first reagent bottle 179. The robotic arm 190 then maneuvers the hydropneumatic aspiration and dispensing head 216 to pick up a new pipette tip 134 from the rack 127, and to check the reagent level in the next reagent bottle 180 in the holder 166. The new pipette tip 134 is then discarded, and the process is repeated for the remaining two reagent bottles 181 and 182. By using a new disposable pipette tip 134 for each of the reagent bottles 179–182, cross-contamination among different reagents is avoided.

In FIG. 14E, the hydropneumatic aspiration and dispensing head 216 is shown after having picked up a new disposable pipette tip 134 from the station 126. The head 216 has now been moved to a position above the first sample tube 120, and the pipette tip 134 is lowered into the sample tube 120 until the liquid sample is detected (as before, this is done by operating the head 216 in the liquid detection mode). The liquid sample preferably has a minimum volume of about 250 μL; of this, about 55 μL is drawn up into the pipette tip 134 by aspirating air into the nozzle 218 of the head 216. To prevent a droplet from forming at the bottom of the pipette tip 134 after the tip is removed from the sample tube 120, a transport air gap of about 10 μL is maintained between the tip opening and the bottom level of the liquid sample held in the tip. In general, it will be desirable to maintain a transport air gap in the pipette tip 134 for all liquid transfers that are carried out by the hydropneumatic aspiration and dispensing head 214.

In FIG. 14F, the hydropneumatic aspiration and dispensing head 216 has been moved by the robotic arm 190 to a position above the sample port 304 of the first reaction device 88. The head 216 is then lowered to move the pipette tip 134 into the sample area 308 of the reaction device 88, and the liquid biological sample is discharged into the sample area 308 by dispensing air from the head 216. When this operation is completed, the pipette tip 134 is withdrawn and ejected into the box 144 of FIGS. 3 and 4, and a new pipette tip is picked up from the rack 127. The procedure illustrated in FIGS. 14E and 14F is then repeated in order to transfer the liquid sample from the next sample tube 120 to the next reaction device 88. This sequence is repeated for each of the sample tubes 120 and reaction devices 88, using a new disposable pipette tip 134 each time. When all of the liquid samples have been transferred, the head 216 is moved to the docking station 152 to pick up one of the pneumatic aspiration and dispensing pipettes 164 using the procedure shown in FIGS. 6A and 6B.

In FIG. 14G, the head 216 (now carrying a pneumatic aspiration and dispensing pipette 164 with its resilient tip 234) has been moved to a position above the pneumatic port 310 of the first reaction device 88. The head 216 is then lowered to bring the resilient tip 234 of the pipette 164 into engagement with the pneumatic port 310 of the reaction device 88, and a sufficient amount of air is aspirated from the reaction device to cause the liquid sample to move from the sample area 308 to the decontamination zone 312 of the reaction area 314. This procedure is repeated for each of the reaction devices at the reaction station 78, and for the reaction devices 88 at the remaining reaction stations 80–84, using the same pneumatic aspiration and dispensing pipette 164. Use of the same pipette 164 does not give rise to cross-contamination problems, since the pipette 164 does not make contact with the liquid biological samples within the reaction devices 88.

After the pipette 164 is removed from the pneumatic port 310 of the last reaction device 88, and with the liquid biological samples now received in the decontamination zones 312 of the reaction devices 88, the heating platens 92 and 100 of that reaction station are energized to heat the liquid samples to a temperature of 41° C. This temperature is maintained for an incubation period of 50 minutes, during which the decontamination reaction occurs. This is illustrated in FIG. 14H. The 50-minute incubation periods (and all subsequent decontamination, amplification and assay steps) are staggered among the reaction stations 78–84, with a 16-minute interval (the longest period of time required to carry out any operation at a given reaction station) from one to the next. This insures that the chemical reactions occurring in all of the reaction devices and assay devices are of the same duration, regardless of the reaction station involved.

Following completion of the decontamination reaction at a given reaction station, the robotic arm 190 returns the head 216, with the pneumatic aspiration and dispensing pipette 164 and resilient tip 234, to a position above the pneumatic port 310 of the first reaction device 88. The resilient tip 234 of the pipette 164 is then brought into contact with the pneumatic port 310, as shown in FIG. 14I, and a controlled amount of air is aspirated from the reaction device 88 to cause the liquid biological sample to move from the decontamination zone 312 to the amplification zone 318. This procedure is repeated for all of the remaining reaction devices 88 at the reaction station, using the same pipette 164. When the liquid biological samples in all of the reaction devices 88 at the reaction station have been transferred to the amplification zones, an incubation period of 120 minutes begins, during which the amplification reaction occurs in the amplification zones 318 of the reaction devices 88. This is illustrated in FIG. 14J. At the conclusion of the 120-minute incubation period, the amplification reaction is stopped by operating the heating platens 92 and 100 to raise the temperature of the samples to 80° C. for five minutes. After the five minute heat spike, the fans 226 of FIG. 3 are turned on to cool the heating platens 92 and the platen temperature is reduced to 41° C.

In FIG. 14K, the resilient tip 234 of the pneumatic aspiration and dispensing pipette 164 has again been brought into contact with the pneumatic port 310 of the first reaction device 88 at one of the reaction stations 78–84. A controlled amount of air is dispensed through the pipette 164 by the head 216 to cause the liquid biological sample within the reaction device 88 to move from the amplification zone 318 of the reaction area 314 back to the sample area 308. This procedure is repeated for each of the remaining reaction devices 88 at the reaction station. The state of each reaction device 88 at this point is illustrated in FIG. 14L.

After the liquid biological samples have been returned to the sample areas 308 of the reaction devices 88 at the reaction station, the pneumatic aspiration and dispensing pipette 164 is returned to the docking station 152 of FIGS. 3 and 4 using the procedure shown in FIGS. 6A and 6B. The hydropneumatic aspiration and dispensing head 216 is then moved by the robotic arm 190 to a position above the wash cup 156, as illustrated in FIG. 14M, and a small amount of system fluid is discharged into the wash cup to purge air from the nozzle 218.

In FIG. 14N, the nozzle 218 has been moved to a position above the first well (i.e., the well closest to the row of reaction devices 88) of the first assay device 90 at one of the reaction stations 78–84. A quantity of system fluid is discharged into the well for subsequent mixing with the amplified sample, typically 30 μL recovered from the original 55 μL, from the corresponding reaction device 88. For an amplified sample volume of approximately 30 μL, the volume of system fluid discharged into the first well is approximately 60 μL. Each microwell of the assay device 90 has a capacity of about 400 μL.

Following the discharge of system fluid into the first well of each assay device 90 of the reaction station, the robotic arm 190 moves the hydropneumatic aspiration and dispensing head 216 to a position above the disposable pipette tube rack 127 and picks up a new disposable pipette tip 134. With the tip in place, the head 216 is moved to a position above the sample port 304 of the first reaction device 88, and is then lowered to move the pipette tip 134 into the sample area 308 of the reaction device as illustrated in FIG. 14O. The liquid sample is then aspirated from the reaction device 88 into the disposable pipette tip 134. Because the sample will be transported over a short distance (to the adjacent assay device 90) and will not pass over any other samples, a transport air gap need not be maintained at the bottom of the pipette tip during this transfer.

In FIG. 14P, the robotic arm 190 has moved the hydropneumatic aspiration and dispensing head 216 (with the pipette tip 134 containing the liquid aspirated from the first reaction device 88) to a position above the first microwell of the first assay device 90. The pipette 134 is then lowered into the microwell and the 30 μL of amplified sample is dispensed into the 60 μL of system fluid. Then, 60 μL of the mixture is aspirated into the pipette 134, and the pipette is elevated above the remaining fluid in the microwell. A 30 μL volume of air is aspirated into the pipette tip 134, the 30 μL of air and 60 μL of fluid are dispensed into the microwell, and the pipette tip 134 is again lowered into the microwell to begin a second aspiration. This process is then repeated to insure complete mixing. At this point, the head 216 aspirates 60 μL of the mixture and dispenses 30 μL of the mixed sample into each of the two remaining microwells of the first assay device 90, leaving 30 μL in the first microwell. The pipette tip 134 is then ejected into the box 144 at the pipette tip disposal station 142, a new tip is obtained from the disposable pipette tip station 126, and the sample aspiration, mixing and dispensing procedure is repeated for the next reaction device 88 and assay device 90. This procedure is repeated for each of the remaining reaction devices 88 and assay devices 90 of the reaction station, using a new disposable pipette tip 134 each time, until all of the reacted liquid samples have been removed from the reaction devices 88 and transferred to the microwells of the corresponding assay devices 90.

After the liquid samples at the last reaction station 84 have been transferred to the assay devices 90, the hydropneumatic aspiration and dispensing head 216 ejects the last used pipette tip 134 at the tip disposal station 142 and picks up a new tip from the disposable pipette tip station 126. With the new tip 134 in place, the head 216 is carried by the robotic arm 190 to the reagent station 154, where a quantity of a first hybridization reagent is aspirated into the pipette tip from the lowermost reagent bottle 179. The first hybridization reagent is a signature reagent which detects whether any nucleic acid amplification has occurred in the sample. The position of the hydropneumatic aspiration and dispensing head 216 at this point is the same as indicated in FIG. 14C. The robotic arm 190 then returns the head 216 to the first reaction station 78 and dispenses the reagent into the first (innermost) microwell of the first assay device 90. This procedure is repeated (using the same disposable tip 134) for the first microwell of each of the remaining assay devices 90, with the head 216 returning to the reagent bottle 179 each time that a microwell is filled. After the first microwells of all of the assay devices 90 have been filled with the first hybridization reagent, the hydropneumatic aspiration and dispensing head 216 ejects the used pipette tip 134 in the box 144 and obtains a new tip 134 from the pipette tip station 126. With the new tip 134 attached, the head 216 aspirates a second hybridization reagent from the next reagent bottle 180 and transfers the reagent to the second (middle) microwell of the first assay device 90. The second hybridization reagent is a genus reagent which detects whether a mycobacterial DNA sequence has been amplified. Again, using the same disposable pipette tip 134, this procedure is repeated in order to dispense the second hybridization reagent from the second reagent container 180 to the second microwell of each of the remaining assay devices 90 at the reaction station. After ejecting the used pipette tip 134 and picking up a new pipette tip, the procedure is repeated once again in order to dispense the third hybridization reagent from the third reagent container 181 into the third (outermost) microwell of each assay device 90. The third hybridization reagent is a species reagent that detects any tubercle bacillus DNA sequences in the amplified sample.

At this point, the diluted liquid samples in the first, second and third microwells of each assay device 90 at the reaction station contain the first, second and third hybridization reagents, respectively. An incubation period of 50 minutes then commences, during which the heating platen 94 located beneath the assay devices 90 is controlled to raise the temperature of the liquid samples to 33° C. After the incubation period, the heating platen 94 is deactivated and a wash step is carried out by the wash head 194 to remove the liquid samples and reagents from the microwells of the assay devices 90, leaving only the reacted material which is bound to the inside walls of the assay device wells. Prior to the wash step, the wash head 194 is moved by the robotic arm 192 to a position above the wash cup 156, as shown in FIG. 14Q. Wash fluid is then dispensed from the dispensing nozzles 246 of the wash head 194 in order to purge the dispensing nozzles of air. The robotic arm 192 then moves the wash head 194 to a position above the first assay device 90, and the pumps 222 of FIG. 3 are turned on. The robotic arm 192 then slowly lowers the nozzles 246 and 248 into the microwells of the assay device, as shown in FIG. 14R. In this position, the ends of the aspiration nozzles 248 of the wash head 194 are very close to the bottom surfaces of the microwells, and due to their inclination are directed toward the periphery of the microwells. The sample and reagent fluids are then aspirated from the microwells of the first assay device 90. By slowly moving the wash head 214 downward while aspirating the sample and reagent fluids, actual wetting of the aspiration nozzles 248 by these fluids (and consequent cross-contamination between samples) is avoided. Nozzle wetting is also avoided by maintaining a relatively high aspiration rate through the nozzles 248, since the resulting high-velocity airflow around the nozzles prevents the aspirated fluids from touching the nozzle surfaces directly.

After aspirating the sample and reagent fluids, the wash head 194 is moved slightly upward and toward the center of the microwells in order to separate the aspirating nozzles 246 from the bottom of the microwells of the assay device 90. The wash head 194 is then raised to a dispensing height, as shown in FIG. 14S, and wash fluid is dispensed into the microwells of the assay device 90 from the dispensing nozzles 246. The wash head 194 is then moved to each of the remaining assay devices 90 at the reaction station and repeats the same operations. Wash fluid is dispensed into and aspirated from the microwells of the assay devices 90 two more times, with the wash head 214 moving between the positions shown in FIGS. 14R and 14S during each assay device washing operation. After the last aspiration cycle, the microwells of the assay device 90 are substantially empty except for the amplicons bound to the walls of the microwells. The washing procedure is carried out on each of the assay devices 90 at the reaction station, with each of the aspiration/dispensing cycles occurring at all of the assay devices 90 in succession to provide a soak time for the wash fluid between successive cycles.

When the washing of all of the assay devices 90 at a given assay station is complete, the wash head 194 is returned to the home position (shown in FIG. 3) by the robotic arm 192. The robotic arm 190 then causes the hydropneumatic aspiration and dispensing head 216 to move to a position above the wash cup 156 and dispense a small amount of system fluid in order to purge air from the nozzle 218. The hydropneumatic aspirating and dispensing head 216 then moves to a position above the first microwell of the first assay device 90, and dispenses a small amount of system fluid into the well. The position of the head 216 at this point is the same as illustrated in FIG. 14N. The head 216 then proceeds to dispense system fluid into each of the remaining wells of the first assay device 90, and into the wells of all of the remaining assay devices 90 at the reaction station.

With a small amount of system fluid now present in the microwells of all of the assay devices 90 at the reaction station, the hydropneumatic aspiration and dispensing head 216 picks up a new pipette tip from the pipette tip station 126 and moves to a position above the chemiluminescent reagent bottle 182 at the reagent station 154. Using the pipette tip 134, the head 216 then draws a quantity of chemiluminescent reagent from the fourth reagent bottle 182, as illustrated in FIG. 14T. The head 216 then returns to the first assay device 90 and dispenses an equal amount of the chemiluminescent reagent into the first, second and third microwells of the assay device 90. This procedure is repeated for each of the remaining assay devices 90 at the reaction station with the head 216 returning to the reagent bottle 182 after each assay device 90 is filled. The pipette tip 134 is replaced each time that 12 microwells (i.e., 4 assay devices 90) have been filled, to prevent bubbles from forming as a result of accumulated residual liquid in the pipette tip. The wells of all of the assay devices 90 at the reaction station now contain the chemiluminescent reagent mixed with the system fluid dispensed previously, and the heating platen 94 is now operated to incubate the chemiluminescent reagent in the assay devices at 37° C. for 30 minutes.

When the foregoing sequence of operations has been completed for each of the reaction stations 78–84, the automated portion of the nucleic acid assay is complete. The trays 86 are now be removed from the reaction area 66 of the cabinet 22, and placed in the luminometer 43 of FIG. 1. The function of the luminometer 43 is to detect luminescence within each microwell of each assay device 90, as will occur when the chemiluminescent reagent reacts with the hybridized amplified material which has become bound to the interior walls of the assay devices 90. Such luminescence indicates that a target nucleic acid sequence has been detected. The luminometer is preferably a Model ML 2200 luminometer manufactured by Dynatech Laboratories of Chantilly, Va.

Figure 15:
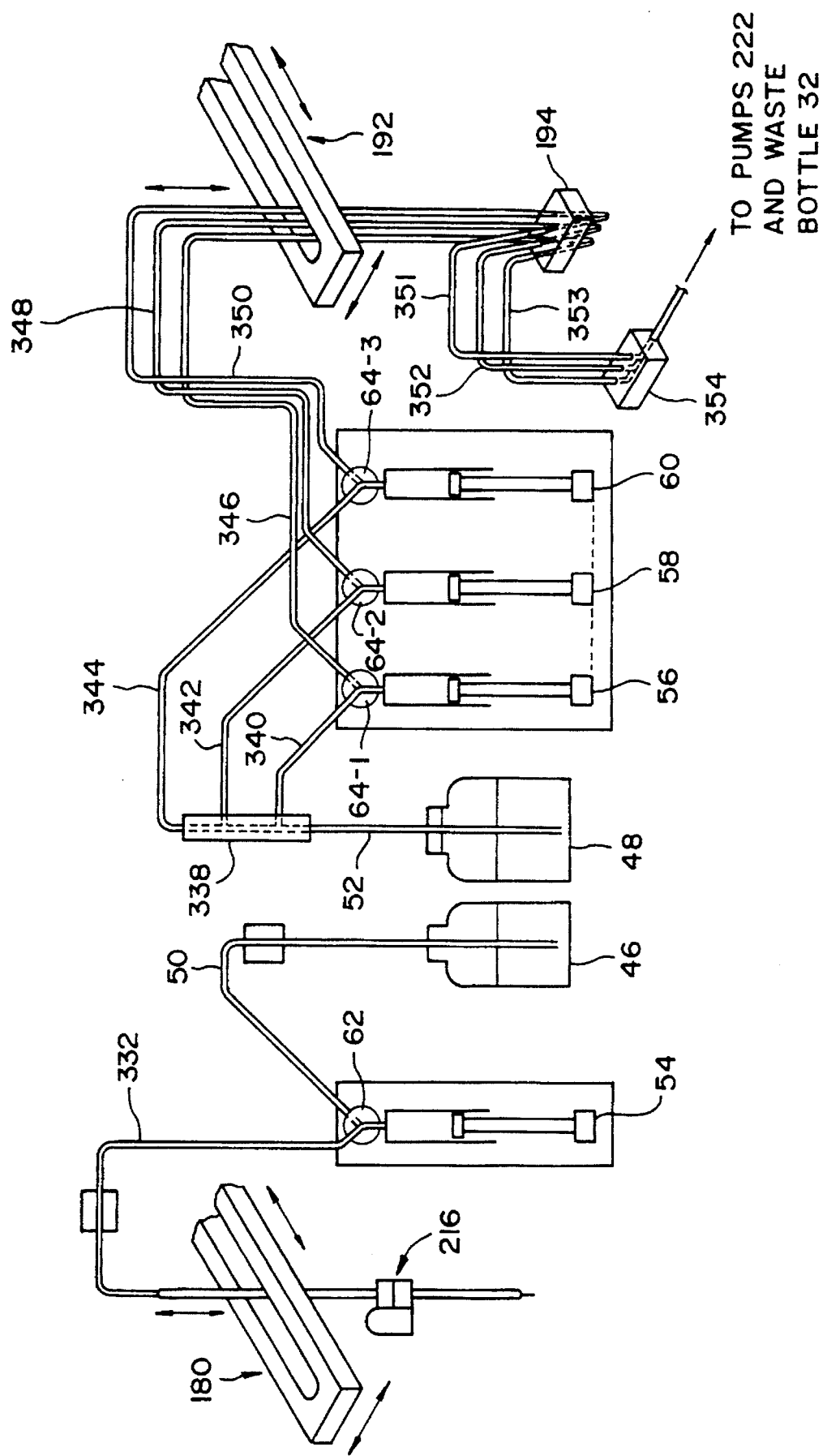
FIG. 15 is a block diagram of the principal fluidic and pneumatic components of the automated assay system.

FIG. 15 is a schematic diagram of the principal pneumatic and fluidic components of the system 20, illustrating the manner in which they are interconnected. The supply bottle 46 containing system fluid is coupled by means of the flexible tube 50 to one port of the control valve 62, which is in turn connected to the syringe pump 54. The second port of the valve 62 is connected to the hydropneumatic aspiration and dispensing head 216 by means of a tube 332. Depending upon the position of the valve 62, the syringe 54 is connected either to the system fluid supply bottle 46 (to fill the syringe) or to the hydropneumatic aspiration and dispensing head 216 (to dispense or aspirate air, or to dispense system fluid). The wash fluid supply bottle 48 is connected by means of the tube 52 to a three-way coupling or manifold 338, the outputs of which are connected to the ganged control valves 64-1, 64-2 and 64-3 via tubes 340, 342 and 344, respectively. The control valves 64-1, 64-2 and 64-3 are coupled to the respective syringes 56, 58 and 60 and to corresponding output tubes 346, 348 and 350, respectively. Depending upon the position of the control valves 64-1 through 64-3, the syringes 56–60 either draw fluid from the wash fluid supply bottle 48 (to fill the syringes) or dispense the wash fluid to the wash head 194 through the tubes 346–350. The tubes 346–350 are coupled to the wash head dispensing nozzles 246 of FIGS. 7A and 7B and additional tubes 351, 352 and 353 couple the wash head aspiration nozzles 248 of FIGS. 7A and 7B to the pumps 222 and waste bottle 32 through a three-way coupling or manifold 354.

Figure 16:
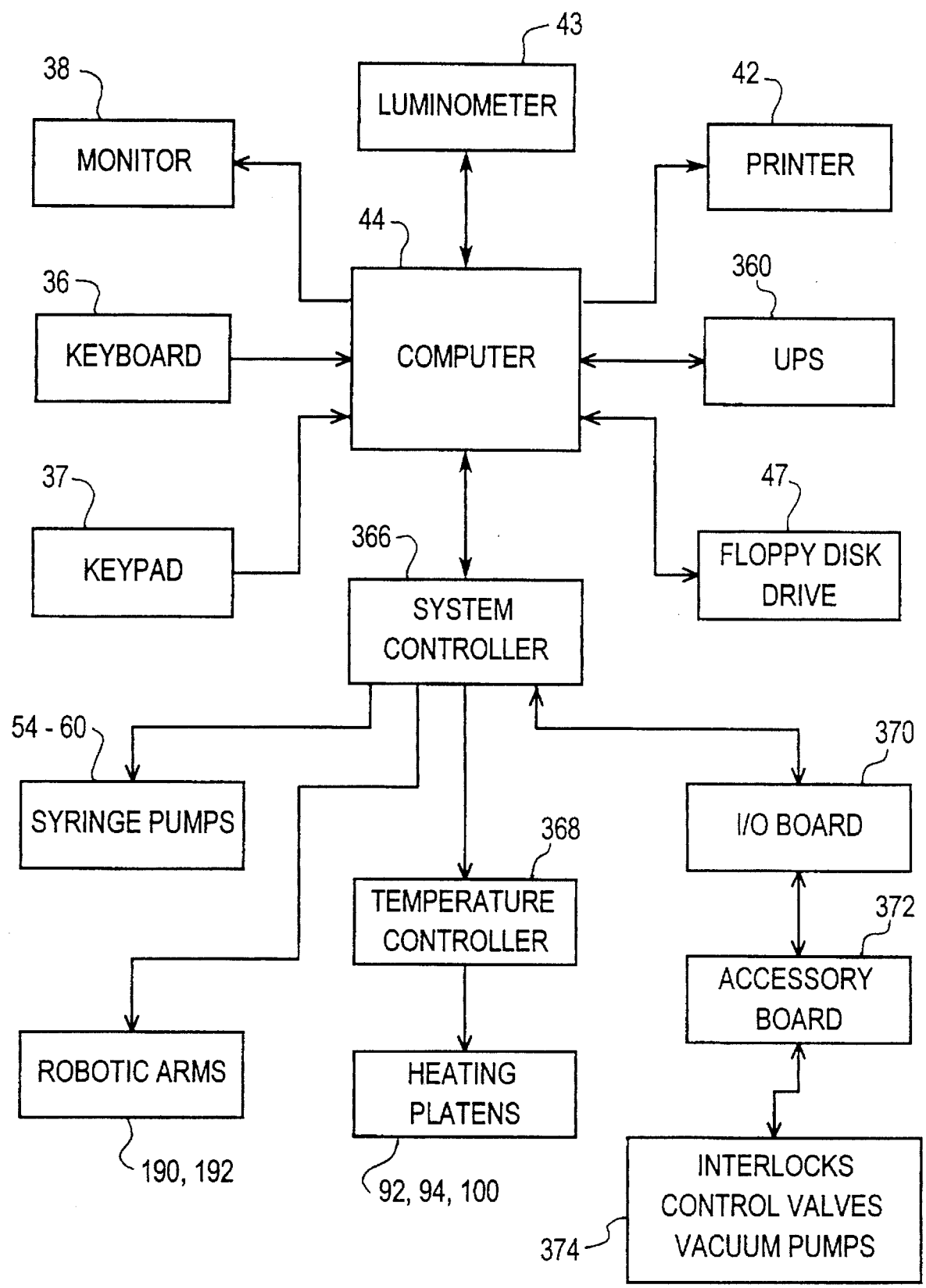
FIG. 16 is a block diagram of the principal electrical components of the automated assay system.

FIG. 16 is a block diagram illustrating the principal electrical components of the system 20. The system computer 44 is connected to the keyboard 36, numeric keypad 37, monitor 38, and printer 42 of FIG. 1, and also to the floppy disk drive 47 and luminometer 47. The floppy disk drive 362 allows control programs to be loaded into the computer 44 (including software updates), and also allows assay results to be stored on floppy disks. The luminometer 43, which receives the assay devices 90 after they are removed from the cabinet 22 of the system 20, is also connected to the computer 44 (via a serial card) so that the final results of the assay can be logged automatically. An uninterruptible power supply (UPS) 360 provides power to the system components and has a logic connection to the computer 44 to allow for orderly system shut-down in the event of a power failure.

The computer 44 controls the functions of the system 20 through a system controller 366. The system controller 366 is connected to the syringe pumps 54–60 of FIGS. 2 and 15, to the robotic arms 190 and 192 of FIG. 3, and to a temperature control circuit 368 which regulates the temperatures of the heating platens 92, 94 and 100 and switches the fans 226 on and off. The system controller 366 is also connected by means of an input/output board 370 and an accessory board 372 to various other components of the system 20, including the control valves 62 and 64-1 through 64-3, pumps 222, and interlocks for the doors 24 and 29 and pivotable arms 102. These components are represented collectively by the block 374 in FIG. 16.

Figure 17:
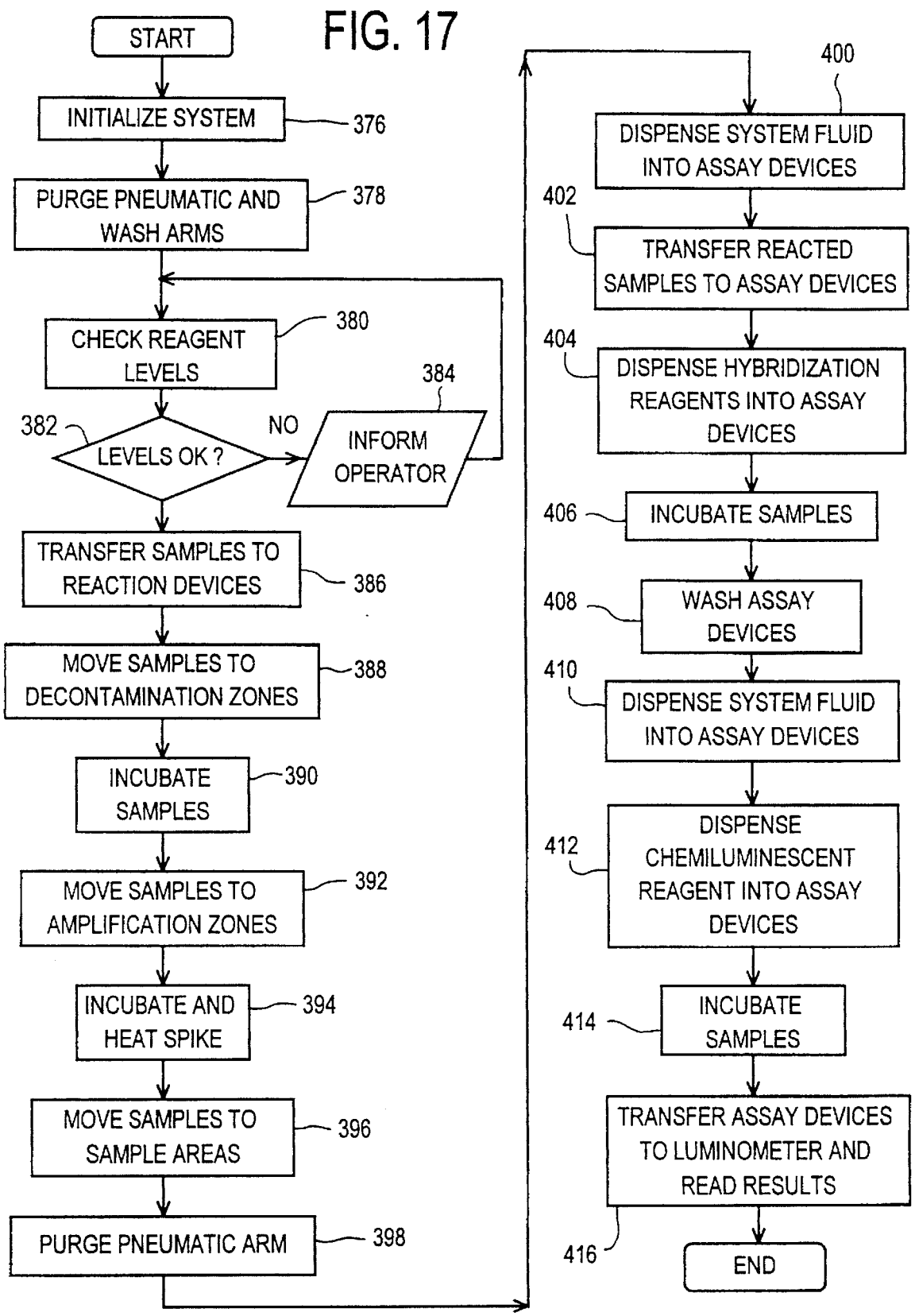
FIG. 17 is a flow chart illustrating the sequence of operations carried out by the computer shown in the block diagram of FIG. 16.

FIG. 17 is a flow chart which summarizes the operations carried out by the system computer 44 of FIG. 16 in executing the motions illustrated in FIGS. 14A–14T at each of the reaction stations 78–84. Following start-up, an initialization procedure is carried out in block 376 to allow the operator to specify the desired values of certain system parameters. These include transport air gap volume, aspiration and dispensing volumes and speeds, incubation times, and number of samples and controls. Following initialization, the computer proceeds to block 378 and purges the wash head 194 and hydropneumatic aspiration and dispensing head 216 of air. The levels of the four liquid reagents are then checked in blocks 380 and 382, and any inadequate reagent levels are brought to the attention of the operator in block 384 by producing an output on the video display monitor 338. If the reagent levels are found to be adequate, the system proceeds to block 386 and transfers the liquid biological samples from the sample tubes 120 to the reaction devices 88 using the hydropneumatic aspiration and dispensing head 216 and the disposable pipette 134. When this is complete, the system proceeds to block 388 and uses one of the two pneumatic aspiration and dispensing pipettes 164 to move the samples to the decontamination zones 312 of the reaction devices 88. This is followed by the an incubation period in block 390, during which decontamination takes place. In block 392, the pneumatic aspiration and dispensing pipette 164 is used once again to move the liquid samples to the amplification zones 318 of the reactions devices 88, and this is followed by a further incubation period and heat spike in block 394. When amplification is complete, the liquid samples are moved back to the sample areas 308 of the reaction devices 88 as indicated in block 396. With the pipette 164 restored to the docking station 152, the hydropneumatic aspiration and dispensing head 216 is purged in block 398, and system fluid is then dispensed into the first well of each assay device 90 in block 400. In block 402, the reacted liquid samples are transferred from the reaction devices 88 to the assay devices 90 using the disposable pipette tips 134, and are mixed with system fluid in the manner described previously. In block 404, the three hybridization reagents are dispensed sequentially from the reagent bottles 179–181 into the corresponding wells of the assay devices 90, and this is followed by an incubation period in block 406 and by washing and aspiration of the assay devices 90 in block 408. In blocks 410 and 412, system fluid and chemiluminescent reagents are dispensed into the assay devices 90. This is followed by an incubation period in block 414. After incubation, the assay devices are manually transferred to the luminometer 43 of FIGS. 1 and 16. In block 416, the output of the luminometer 43 (representing the final results of the assay) are read by the computer 44 and are displayed to the user via the monitor 38 and printer 42. The assay procedure is now complete, and the subsequent assays may be carried out by re-initializing the system in the manner described previously.

A number of modifications may be made to the automated assay system 20, in addition to those already described. With reference to FIGS. 3 and 4, one possible modification comprises a rearrangement of the reaction area 66 to relocate the pipette tip disposal station 142 from the position shown to a new position on the right side of the reagent station 154. This may be preferable in that it provides greater separation between the hydropneumatic aspiration and dispensing head 216 and the sample tube rack 110 when the head 216 is ejecting a used pipette tip 134, thereby lessening the chances of cross-contamination due to airborne droplet generation by the ejected tip. The reagent bottle holder 166 may be reduced in size (e.g., by eliminating the cap cavities 178) in order to accommodate the new location of the pipette tip disposal station 142.

As another modification, the hydropneumatic aspiration and dispensing head 216 may be modified so that a disposable pipette tip 134 and a pneumatic aspiration and dispensing pipette 164 can be carried by the head 216 at the same time. In this modification, the disposable pipette tip 134 and pneumatic aspiration and dispensing pipette 164 are preferably separated from each other by a distance corresponding to the distance between the sample tower 262 and pneumatic tower 266 of a reaction device 88. This allows a disposable pipette tip 134 to be introduced into the sample tower 262 at the same time as the resilient tip 234 of the pneumatic aspiration and dispensing pipette 164 is brought into contact with the pneumatic tower 266. Appropriate changes may also be made in the fluidic aspiration and dispensing system of FIG. 15 to allow the disposable pipette tip 134 and pneumatic aspiration and dispensing pipette 164 to be operated independently of each other.

Figure 18:
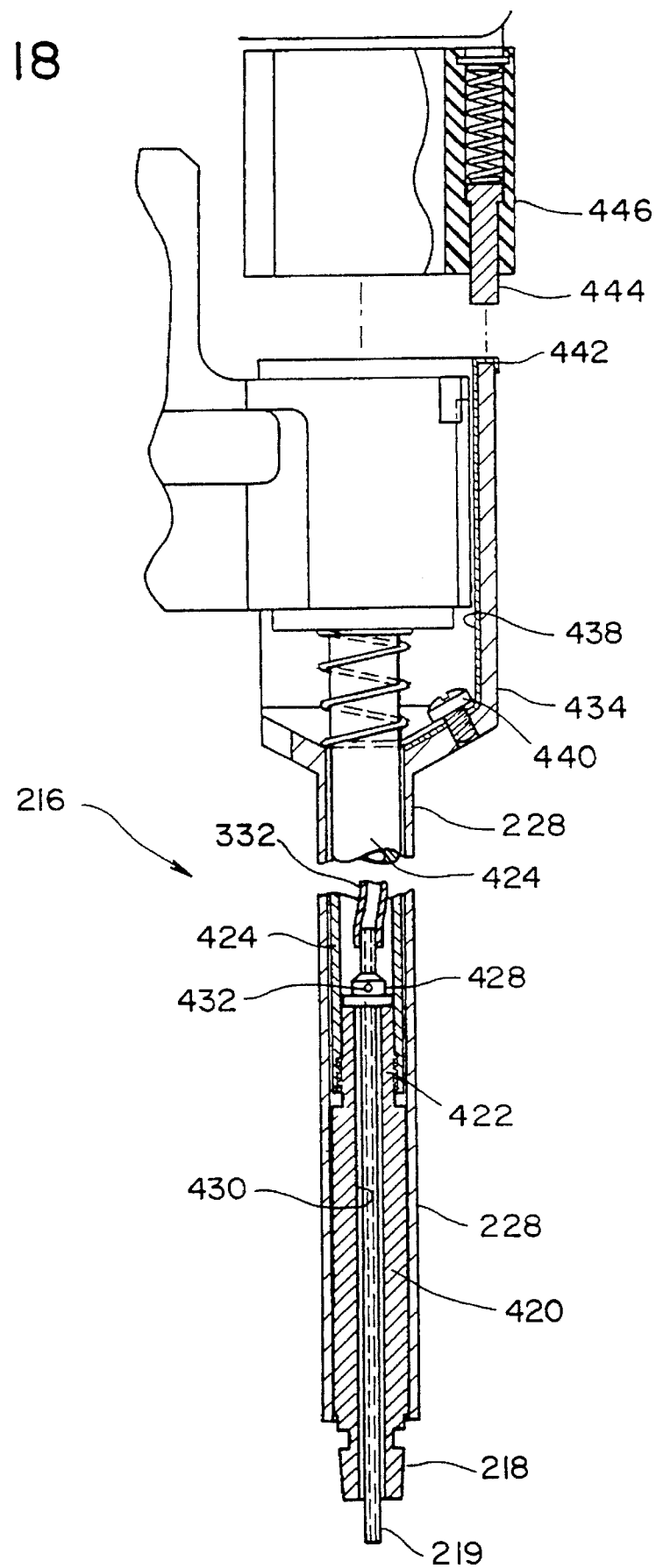
FIG. 18 illustrates the details of the hydropneumatic aspiration and dispensing head that is carried by the robotic arm of FIG. 3.

FIG. 18 illustrates the details of the hydropneumatic aspiration and dispensing head 216 that is carried by the robotic arm 190 of FIG. 3. The construction shown represents a modification of the basic TECAN design, and is the embodiment preferred for use in the present invention. The metal tip 218 is an extension of an elongated metal cylinder 420 which is threadably engaged at its upper end 422 with a hollow rod 424. A length of hypodermic tubing 426 passes through an axial bore 430 in the metal cylinder 420, and projects through the tip 218 to form the aspiration and dispensing nozzle 219 referred to previously. A flange 428 is formed near the upper end of the tube 426 to hold the tube in place with respect to the metal cylinder 420. The flexible tube 332 of FIG. 15 is attached to the upper end of the tube 426 to provide hydropneumatic aspiration and dispensing through the nozzle 219. The tube 426 fits loosely within the bore 430, and the annular space between the outside of the tube 426 and the inside of the bore 430 forms an air passage for the liquid detection function of the TECAN system. At its bottom end, the air passage terminates in an annular outlet (not visible in FIG. 18) which surrounds the nozzle 219 at the bottom face of the tip 218. At its upper end, the air flow passage terminates in a lateral bore 432 formed near the upper end of the metal cylinder 420. The lateral bore 432 communicates with the hollow interior of the tube 424, in which an air flow is maintained by the liquid detection system (not shown) of the TECAN unit.

With continued reference to FIG. 18, it will be observed that the metal cylinder 420 and hollow tube 424 are both received in the slidable ejector sleeve 228 described previously. At its upper end, the ejector sleeve 228 is expanded to form a partially cylindrical structure 434 whose upper end 436 is displaced downwardly when the robotic arm 190 is moved to the upper limit of its travel in the z direction. An electrically conducting strip 438 is attached by means of a screw 440 to the interior surface of the cylindrical structure 434 and terminates in a U-shaped contact 442 which fits over the upper edge of the cylindrical structure 434 as shown. As the robotic arm 190 approaches its uppermost position, the contact 442 is brought into contact with a conductive, spring-loaded plunger 444. Appropriate electrical circuitry (not shown) detects electrical continuity between the contact 442 and plunger 444 to determine that the robotic arm is near its uppermost position. Further upward travel of the robotic arm will cause the upper edge of the cylindrical structure 434 to be brought in contact with a fixed abutment 446 in which the plunger is mounted, thereby displacing the cylindrical structure 434 and ejector sleeve 228 downwardly to eject a disposable pipette tip 134 in the manner described previously.

The foregoing is illustrative of the present invention, and is not to be construed as limiting thereof, as numerous alternatives to the devices and methods described which incorporate the present invention will be apparent to those skilled in the art. The invention is accordingly defined by the following claims, with equivalents of the claims to be included therein.

What is claimed is:

1. An automated system for carrying out reactions on a plurality of liquid samples, comprising:

a plurality of reaction devices in which said liquid samples are receivable, each of said reaction devices including a sample area for receiving a liquid sample, a reaction area separate from said sample area into which said liquid sample is movable from said sample area to carry out a reaction on said sample, and a pneumatic port for allowing air to be aspirated from and dispensed into said reaction device to move said liquid sample between said sample area and said reaction area;

a reaction station adapted to hold said plurality of reaction devices;

a robotically controlled aspiration and dispensing head adapted to move into contact with said pneumatic ports of said reaction devices, and to aspirate air from and dispense air into said pneumatic ports in order to move the liquid samples in said reaction devices between said sample areas and said reaction areas; and a programmable control device for causing said robotically controlled aspiration and dispensing head to move into contact with said pneumatic ports of said reaction devices, and to withdraw air from and dispense air into said reaction devices in order to move said liquid samples between said sample areas and said reaction areas.

2. An automated system as claimed in claim 1, wherein said robotically controlled aspiration and dispensing head is adapted to be brought into contact with the pneumatic port of only one of said reaction devices at a time, and wherein said programmable control device causes said robotically controlled aspiration and dispensing head to move into contact with each of said reaction devices in sequence.

3. An automated system as claimed in claim 1, wherein said robotically controlled aspiration and dispensing head carries a detachable pipette for engaging the pneumatic ports of said reaction devices, and wherein said system further comprises a docking station for holding said detachable pipette when said pipette is not attached to said robotically controlled aspiration and dispensing head.

4. An automated system as claimed in claim 3, wherein said programmable control device causes said robotically controlled aspiration and dispensing head to pick up said detachable pipette from said docking station before moving into contact with the pneumatic ports of said reaction devices, and to return said detachable pipette to said docking station after withdrawing air from and dispensing air into said reaction devices.

5. An automated system as claimed in claim 4, wherein said docking station includes a bracket with which said detachable pipette is engageable by means of a generally horizontal motion of said robotically controlled aspiration and dispensing head, said pipette being detachable from said aspiration and dispensing head by means of a generally upward motion of said aspiration and dispensing head while said pipette is engaged with said bracket.

6. An automated system as claimed in claim 1, wherein said programmable control device causes said robotically controlled aspiration and dispensing head to move said liquid samples from said sample areas to said reaction areas, to allow said liquid samples to remain in said reaction areas for predetermined intervals, and to return said liquid samples to said sample areas after said predetermined intervals have elapsed.

7. An automated system as claimed in claim 6, wherein said predetermined intervals are equal for all of said reaction devices.

8. An automated system as claimed in claim 1, further comprising:
   a disposable pipette tip station adapted to hold a plurality of disposable pipette tips which are individually attachable to said robotically controlled aspiration and dispensing head; and
   a sample receptacle station adapted to hold a plurality of sample receptacles in which said liquid samples are initially provided;
   wherein said programmable control device causes said robotically controlled aspiration and dispensing head to pick up disposable pipette tips from said disposable pipette tip station, to move to said sample receptacle station and aspirate liquid samples into said disposable pipette tips from said sample receptacles, and to move to said reaction station and dispense said liquid samples into said reaction devices.

9. An automated system as claimed in claim 8, wherein said robotically controlled aspiration and dispensing head is adapted to pick up only one of said disposable pipette tips at a time, and wherein said programmable control device causes said robotically controlled aspiration and dispensing head to move to said disposable pipette tip station and to pick up a new disposable pipette tip before aspirating a liquid sample from each of said sample receptacles.

10. An automated system as claimed in claim 1, further comprising:
    a disposable pipette tip station adapted to hold a plurality of disposable pipette tips which are individually attachable to said robotically controlled aspiration and dispensing head; and
    a reagent station adapted to hold a plurality of reagent containers which contain liquid reagents to be added to said liquid samples;
    wherein said programmable control device causes said robotically controlled aspiration and dispensing head to pick up disposable pipette tips from said disposable pipette tip station, to move to said reagent station and aspirate liquid reagents into said disposable pipette tips from said reagent containers, and to move to said reaction station and dispense said liquid reagents into said liquid samples.

11. An automated system as claimed in claim 10, wherein said robotically controlled aspiration and dispensing head is adapted to pick up only one of said disposable pipette tips at a time, and wherein said programmable control device causes said robotically controlled aspiration and dispensing head to move to said disposable pipette tip station and pick up a new disposable pipette tip before aspirating a liquid reagent from each of said reagent containers.

12. An automated system as claimed in claim 10, wherein said reaction station is adapted to hold a plurality of assay devices to which said liquid samples are transferred after reactions are carried out on said samples in said reaction devices, and wherein the dispensing of said liquid reagents into said liquid samples is carried out by dispensing said reagents into said assay devices.

13. An automated system as claimed in claim 12, wherein prior to aspiration and dispensing of said liquid reagents into said assay device, said programmable control device causes said robotically controlled aspiration and dispensing head to pick up disposable pipette tips from said disposable pipette tip station, to move to said reaction station and aspirate reacted liquid samples from said reaction devices, and to dispense said reacted liquid samples into said assay devices.

14. An automated system as claimed in claim 13, wherein said robotically controlled aspiration and dispensing head is adapted to pick up only one of said disposable pipette tips at a time, and wherein said programmable control device causes said robotically controlled aspiration and dispensing head to move to said disposable pipette tip station and pick up a new disposable pipette tip before aspirating a reacted liquid sample from each of said reaction devices.

15. An automated system as claimed in claim 12, wherein each of said assay devices includes a plurality of separate portions, each of said portions being adapted to receive part of the same liquid sample, and wherein the dispensing of said reagents into each of said assay devices is carried out by dispensing a different one of said reagents into each portion of said assay device.

16. An automated system as claimed in claim 12, further comprising a robotically controlled wash head adapted to dispense a wash fluid into said assay devices and to aspirate fluids from said assay devices, said robotically controlled wash head being controlled by said programmable control device.

17. An automated system as claimed in claim 16, wherein each of said assay devices includes a plurality of separate portions, each of said portions being adapted to receive part of the same liquid sample, and wherein said robotically controlled wash head includes separate aspiration/dispensing nozzles for washing all of said portions simultaneously.

18. An automated system as claimed in claim 12, wherein each of said assay devices is held adjacent to a corresponding one of said reaction devices at said reaction station, with the number of assay devices and reaction devices being equal.

19. An automated system as claimed in claim 18, wherein said assay devices and said reaction devices are carried by a tray which is removable from said automated system.

20. An automated system as claimed in claim 1, wherein said reaction station includes a heating platen for heating said plurality of reaction devices.

21. An automated system as claimed in claim 1, wherein said reaction station is one of a plurality of reaction stations in said automated system, and wherein said programmable control device causes said robotically controlled aspiration and dispensing head to carry out substantially the same functions at each of said reaction stations.

* * * * *